(12) United States Patent
Labhasetwar

(10) Patent No.: US 8,507,437 B2
(45) Date of Patent: Aug. 13, 2013

(54) APOPTOSIS-MODULATING P53 PROTEIN THERAPY FOR VASCULAR DISORDERS AND NANOPARTICLES CONTAINING THE SAME

(75) Inventor: Vinod Labhasetwar, Solon, OH (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/019,385

(22) Filed: Feb. 2, 2011

(65) Prior Publication Data

US 2011/0130325 A1 Jun. 2, 2011

Related U.S. Application Data

(62) Division of application No. 12/170,127, filed on Jul. 9, 2008, now abandoned.

(60) Provisional application No. 60/958,830, filed on Jul. 9, 2007.

(51) Int. Cl.
| | | |
|---|---|---|
| *A61K 31/765* | (2006.01) | |
| *A61K 38/16* | (2006.01) | |
| *A61K 9/00* | (2006.01) | |
| *C07K 14/435* | (2006.01) | |

(52) U.S. Cl.
USPC .......... 514/16.4; 977/705; 530/350; 530/300; 514/18.9

(58) Field of Classification Search
None
See application file for complete search history.

(56) References Cited

U.S. PATENT DOCUMENTS

| 6,491,922 | B1 * | 12/2002 | Ho |
| 7,297,685 | B2 * | 11/2007 | Ferran et al. |
| 7,332,159 | B2 | 2/2008 | Labhasetwar et al. |
| 2006/0251726 | A1 | 11/2006 | Lin et al. |

OTHER PUBLICATIONS

Scott et al., Human Vascular Smooth Muscle Cells from Restenosis or In-Stent Stenosis Sites Demonstrate Enhanced Responses to P53. Implications for Brachytherapy and Drug Treatment for Restenosis, Circulation Research, 90(4), 398-404, 2002.*
Labhsetwar et al., Arterial uptake of biodegradable nanoparticles: effect of surface modifications, J. Pharm. Sci. 87(10):1229-1234, 1998.*
Jacobs et al., A nanotechnology-based delivery system: Nanobots. Novel vehicles for molecular medicine, J. Cardiovasc. Surg. 52(2):159-167, Apr. 2011.*
Kojima et al., Role of a p53 polymorphism in luminal narrowing after coronary balloon angionplasty, J. Am. College Cardiol. 37(2) Suppl. A, pp. 66A, abstract 1223-35, Feb. 2001.*
Benchimol, S., p53—An examination of sibling support in apoptosis control, Cancer Cell, 6(1):3-4, Jul. 2004.*
Aoki, M., et al. "Inhibition of the p53 tumor suppressor gene results in growth of human aortic vascular smooth muscle cells. Potential role of p53 in regulation of vascular smooth muscle cell growth." Hypertension. Aug. 1999;34 (2):192-200.
Aranda-Anzaldo A., et al. "p53 is a rate-limiting factor in the repair of higher-order DNA structure." Biochim Biophys Acta. Sep. 3, 1999;1446(3):181-92.

(Continued)

*Primary Examiner* — Claire Kaufman
(74) *Attorney, Agent, or Firm* — Patrick J. Hagan; Dann, Dorfman, Herrell and Skillman, P.C.

(57) ABSTRACT

Protein containing nanoparticles and methods of use thereof for the treatment of proliferative disorders are disclosed.

12 Claims, 4 Drawing Sheets

Schematic representing the localization of NPs in the arterial wall

(56) References Cited

OTHER PUBLICATIONS

Bedi, A., et al. "Biological significance and molecular mechanisms of p53-induced apoptosis." Apoptosis. Sep. 1998;3 (4):237-44.
Bennett, M., et al. "Cell surface trafficking of Fas: a rapid mechanism of p53-mediated apoptosis." Science. Oct. 9, 1998;282(5387):290-3.
Blagosklonny, M., et al. "p53 from complexity to simplicity: mutant p53 stabilization, gain-of-function, and dominant-negative effect." FASEB J. Oct. 2000;14(13):1901-7.
Dubrez, L., et al. "Cell cycle arrest is sufficient for p53-mediated tumor regression." Gene Ther. Nov. 2001;8 (22):1705-12.
Ehrhardt, H., et al. "Cytotoxic drug-induced, p53-mediated upregulation of caspase-8 in tumor cells." Oncogene. Jan. 31, 2008;27(6):783-93. Epub Jul. 16, 2007.
el-Deiry, W. S., et al. "WAF1, a potential mediator of p53 tumor suppression." Cell. Nov. 19, 1993;75(4):817-25.
Guevara, N. V., et al. "The absence of p53 accelerates atherosclerosis by increasing cell proliferation in vivo." Nat Med. Mar. 1999;5(3):335-9.
Ihling, C., et al. "Co-expression of p53 and MDM2 in human atherosclerosis: implications for the regulation of cellularity of atherosclerotic lesions." J Pathol. Jul. 1998;185(3):303-12.
Itahana, K., et al. "A role for p53 in maintaining and establishing the quiescence growth arrest in human cells." J Biol Chem. May 17, 2002;277(20):18206-14. Epub Mar. 5, 2002.
Kubbutat, M. H., et al. "Keeping an old friend under control: regulation of p53 stability." Mol Med Today. Jun. 1998;4 (6):250-6.
Labhasetwar, V., et al. "Arterial uptake of biodegradable nanoparticles: effect of surface modifications." J Pharm Sci. Oct. 1998;87(10):1229-34.
Libby, P. "Gene therapy of restenosis: promise and perils." Circ Res. Feb. 23, 1998;82(3):404-6.
Lin, D., et al. "Growth arrest induced by wild-type p53 protein blocks cells prior to or near the restriction point in late G1 phase." Proc Natl Acad Sci U S A. Oct. 1, 1992;89(19):9210-4.
Matsushita, H., et al. "Transfection of antisense p53 tumor suppressor gene oligodeoxynucleotides into rat carotid artery results in abnormal growth of vascular smooth muscle cells." Circulation. Mar. 28, 2000;101(12):1447-52.

Morishita, M., et al. "Is the oral route possible for peptide and protein drug delivery?" Drug Discov Today. Oct. 2006;11 (19-20):905-10. Epub Sep. 7, 2006.
Muller, D. W., et al. "The role of proto-oncogenes in coronary restenosis." Prog Cardiovasc Dis. Sep.-Oct. 1997;40 (2):117-28.
Prabha, S., et al. "Nanoparticle-mediated wild-type p53 gene delivery results in sustained antiproliferative activity in breast cancer cells." Mol Pharm. May-Jun. 2004;1(3):211-9.
Sayan, B. S., et al. "p53 is cleaved by caspases generating fragments localizing to mitochondria." J Biol Chem. May 12, 2006;281(19):13566-73. Epub Mar. 10, 2006.
Scheinman, M., et al. "p53 gene transfer to the injured rat carotid artery decreases neointimal formation." J Vasc Surg. Feb. 1999;29(2):360-9.
Takenobu, T., et al. "Development of p53 protein transduction therapy using membrane-permeable peptides and the application to oral cancer cells." Mol Cancer Ther. Oct. 2002;1(12):1043-9.
Tanaka, K., et al. "Effects of human cytomegalovirus immediate-early proteins on p53-mediated apoptosis in coronary artery smooth muscle cells." Circulation. Apr. 6, 1999;99(13):1656-9.
Taniyama, Y., et al. "Local delivery of plasmid DNA into rat carotid artery using ultrasound." Circulation. Mar. 12, 2002;105(10):1233-9.
Yonemitsu, Y., et al. "Transfer of wild-type p53 gene effectively inhibits vascular smooth muscle cell proliferation in vitro and in vivo." Circ Res. Feb. 9, 1998;82(2):147-56.
Bell, H.S., et al. "A p53-derived apoptotic peptide derepresses p73 to cause tumor regression in vivo." J Clin Invest. Apr. 2007;117(4):1008-18. Epub Mar. 8, 2007.
Toutouzas, K., et al. "Inflammation and restenosis after percutaneous coronary interventions." Eur Heart J. Oct. 2004;25(19):1679-87.
Song, et al. "Controlled release of U-86983 from double layer biodegradable matrices: effects of additives on release mechanism and kinetics." J Controlled Release. 1997;45:177-192.
Wang, P., et al. "p53 domains: structure, oligomerization, and transformation." Mol Cell Biol. Aug. 1994;14(8):5182-91.
Bell, S., et al. "p53 contains large unstructured regions in its native state." J Mol Biol. Oct. 4, 2002;322(5):917-27.
Labhasetwar, V., et al. "Nanoparticle drug delivery system for restenosis." Adv. Drug Delivery Rev. 1997;24:63-85.

\* cited by examiner

Schematic representing the localization of NPs in the arterial wall

APOPTOSIS-MODULATING P53 PROTEIN THERAPY FOR VASCULAR DISORDERS AND NANOPARTICLES CONTAINING THE SAME

This application is a Divisional Application of U.S. patent application Ser. No. 12/170,127 filed Jul. 9, 2008 now abandoned which claims priority under 35 U.S.C. §119(e) to U.S. Provisional Application, 60/958,830 filed Jul. 9, 2007, the entire content of which is incorporated herein by reference.

FIELD OF THE INVENTION

The present invention relates to the fields of drug delivery and proliferative disorders. More specifically, the invention provides p53 protein containing nanoparticles and methods of use thereof for the treatment of diseases associated with aberrant p53 functions, including without limitation, restenosis, tumor growth, for modulating drug effects which are dependent on p53 functional activity (e.g., drug resistance in cancer therapy), and altered artherogenesis.

BACKGROUND OF THE INVENTION

Several references and patent documents are cited throughout this application to better define the state of the art to which the invention pertains. Each of these citations is incorporated by reference herein as though set forth in full.

Gene delivery using non-viral systems such as liposomes and cationic lipid- or polymer-DNA complexes is usually transient and requires repeated delivery of the expression vector for the maintenance of a therapeutic level of the expressed protein in the target tissue (Li, S., Huang, L., (2000) Gene Ther. 7:31-34; Brown, M. D., et al, (2001) Int. J. Pharm. 229:1-21). The frequency of dosing of the expression vector, depending on the particular disease condition, depends on the efficiency of gene expression and the stability of the expressed protein in the tissue (Bonadio, I. et al., (1999), Nat. Med. 5:753-759). Repeated delivery of the vector may cause toxicity, including an inflammatory response and the therapy may not be effective (Maheshwari, A. et al. (2000), Mol. Ther. 2:121-130; Maheshwari, A. et al, (2002), Gene Ther. 9:1075-1084). To avoid these problems, various sustained release gene delivery systems such as polymeric implants and gels are being investigated (Bonadio, I. et al., (1999), Nat. Med. 5:753-759; Maheshwari, A.; et al. (2000), Mol. Ther. 2:121-130; Maheshwari, A. et al, (2002), Gene Ther. 9:1075-1084; Lim, Y. et al., (2000) Pharm. Res. 17: 811-816; Luo, D. at al. (1999) Pharm. Res. 16:1300-1308).

Recently, it has been demonstrated that nanoparticles (NPs) rapidly escape (within 10 min) from the endolysosomal compartment to the cytoplasmic compartment following their intracellular uptake via an endocytic process (Panyam. J. et al., (2002) FASEB J. 16:1217-1226). The escape of nanoparticles was attributed to the reversal of their surface charge from anionic to cationic in the acidic pH of the endolysosomal compartment, causing nanoparticles to interact with the endolysosomal membrane and then escape into the cytoplasmic compartment (Panyam. J. et al., (2002) FASEB J. 16:1217-1226). The rapid escape of nanoparticles from the endolysosomal compartment could protect nanoparticles as well as the encapsulated therapeutic agent from the degradative environment of the endolysosomes (Prabha, S. et al., (2004) Pharm. Res. 21:354-363).

p53 is a well-studied protein, and its regulation is understood to play a significant role in cancer. The loss of p53 function is a very important event in cancer development. Data suggest that the absence of a functional p53 in tumors favors cancer development (Honda et al., (1998) Exp. Hematol. 26(3):188-97; Wiman, (1998) Med. Oncol. 15(4):222-8). p53 mutations are the most common genetic alterations observed in human cancers including lymphomas and leukemias (Shounan et al., (1997) Leukemia 11(10):1641-9; Chene, (2001) Curr. Med. Chem. Anticancer Agents. 1(2): 151-61). It has been also suggested the loss of p53 function also affects the efficacy of anti-cancer drugs. Although several mechanisms are proposed, decreased p53 expression has been shown to result in increased extracellular matrix synthesis (Harisi et al., (2007) Cancer Biol. Ther. 6(8):1240-1246) or P-gp expression (Cavalcanti et al., (2004) Cytometry B Clin. Cytom. 61(1):1-8), thus reducing the drug uptake and hence the efficacy (e.g., doxorubicin).

In addition to cancer, p53 mutations play important role in other proliferative disorders. For example, Prolapsus uteri in pelvic support disorders are common in elderly women. It has been suggested that alterations in collagen synthesis and collagen types are related to this connective tissue disorder. The studies have shown that higher proliferative activity in prolapsus fibroblasts may result from the decreased expression of p53 protein and may lead to a decrease in the synthesis and deposition of extracellular matrix components (Yamamoto et al., (2000) Mech. Ageing Dev. 115(3):175-87). Another proliferative disorder, moyamoya, is a progressive cerebrovascular occlusive disease. It has been suggested that moyamoya disease may result, at least in part, from an abnormal regulation of extracellular matrix metabolism that leads to increased steady state levels of elastin mRNA and elastin accumulation in the initial thickening (Yamamoto et al., (1997) Stroke 28(9):1733-8).

'Reactive species' (RS) of various types are formed in vivo and many are powerful oxidizing agents, capable of damaging DNA and other biomolecules. Increased formation of RS can promote the development of malignancy, and the 'normal' rates of RS generation may account for the increased risk of cancer development in the aged. Hence additional actions of RS must be important, possibly their effects on p53, cell proliferation, invasiveness and metastasis (Halliwell, (2007) Biochem. J. 401(1):1-11).

Genetically manipulated mice with increased, but otherwise normally regulated, levels of Arf and p53 present strong cancer resistance and have decreased levels of ageing-associated damage. These observations extend the protective role of Arf/p53 to ageing, revealing a previously unknown anti-ageing mechanism and providing a rationale for the co-evolution of cancer resistance and longevity (Matheu et al., (2007) Nature. 448(7151):375-9).

Recent strategies have also turned to the p53 family member, p73, which like p53 is a potent inducer of death, but in contrast is rarely lost or mutated in tumors (Bell and Ryan (2007) Cell Cycle 6(16):1995-2000). p63 and p73, members of the p53 family, have been shown to be functionally distinct from p53. Based on gene sequence homologies, a p53 (TP53) gene family become apparent with the addition of the most recently identified p63 (TP73L; formerly TP63) and p73 (TP73) genes to the already known p53 (Kommagani et al., (2007) J. Biol. Chem. 282(41):29847-54). In addition to p73, p21 and p27 are other cell cycle proteins related to p53-mediated cell cycle arrest.

Delivery of wild type p53 encoding nucleic acid using a nanoparticle formulation has been successfully demonstrated, however, this system has certain drawbacks. For example, it is difficult to ensure that enough p53 nucleic acid enters the cell to be subsequently encoded into sufficient levels of functional p53 protein to ameliorate the symptoms of proliferative disease. Additionally, it is unclear whether diseased cells are capable of transcribing and producing protein in an efficient manner. It is an objective the present invention to provide an improvement to existing methods for delivery of p53, or other proteins involved in cellular senescence, to cells.

SUMMARY OF THE INVENTION

In accordance with the present invention, a method for inhibiting restenosis of a blood vessel (e.g., an artery or vein) comprising administering an effective amount of a protein containing nanoparticle via a blood vessel to a subject in need of treatment is provided. In a particular embodiment, the protein is selected from the group consisting of p21, p27, p53, p63, p73 or a functional fragment thereof. In another embodiment, the nanoparticle comprises a biodegradable polymer comprising a poly(lactide-co-glycolide), poly(lactic acid), poly(alkylene glycol), polybutylcyanoacrylate, poly(methylmethacrylate-co-methacrylic acid), polyallylamine, polyanhydride, polyhydroxybutyric acid, or a polyorthoester or a combination thereof. In still another embodiment, the nanoparticle comprises a targeting moiety. In a different embodiment of the invention, the nanoparticle comprises a plasticizer.

In another aspect of the invention, a p53 protein nanoparticle formulation for sustained release of an effective amount of p53 protein said formulation comprising p53 protein, at least one biodegradable polymer, and an inert plasticizer are provided. In another aspect, the formulation further comprises an antioxidant, an anti-infective, an antiseptic, a steroid, a therapeutic peptide, an analgesic, an anti-inflammatory agent, an anticancer agent, a narcotic, an anesthetic, an antiangiogenic agent, a polysaccharide, a vaccine, an antigen, or a nucleic acid. In yet another aspect, the nanoparticle formulations also include a biodegradable polymer comprising a poly(lactide-co-glycolide), poly(lactic acid), poly(alkylene glycol), polybutylcyanoacrylate, poly(methylmethacrylate-co-methacrylic acid), polyallylamine, polyanhydride, polyhydroxybutyric acid, or a polyorthoester. In a further aspect, the nanoparticle formulation comprises a targeting moiety.

The methods of the invention also include managing VSMC inflammation in a patient following angioplasty comprising administering to said patient a therapeutic agent in an effective amount to manage VSMC inflammation. In another embodiment, the therapeutic agent is a protein containing nanoparticle formulation. In yet another embodiment, the protein containing nanoparticle formulation contains a protein or protein fragment set forth in Table I or Table II.

In another aspect of the invention, a protein containing nanoparticle formulation wherein said protein is selected from the group consisting of SEQ ID NO: 1-28 in a pharmaceutically acceptable carrier is provided.

In yet another embodiment, a method of inhibiting inflammation in a patient following angioplasty is provided comprising administering to said patient a protein containing nanoparticle formulation comprising a protein or protein fragment selected from the group consisting of SEQ ID NO: 1-28.

BRIEF DESCRIPTION OF THE DRAWINGS

FIG. 4A: Artery treated with control NPs; FIG. 4B: Artery treated with p53 protein-loaded modified NPs; FIG. 4C: Graph showing intima/media ratio between control and p53 protein treated cells; FIG. 4D: Graph showing lumen area in control vs. p53 protein treated cells.

DETAILED DESCRIPTION OF THE INVENTION

Figure 1:
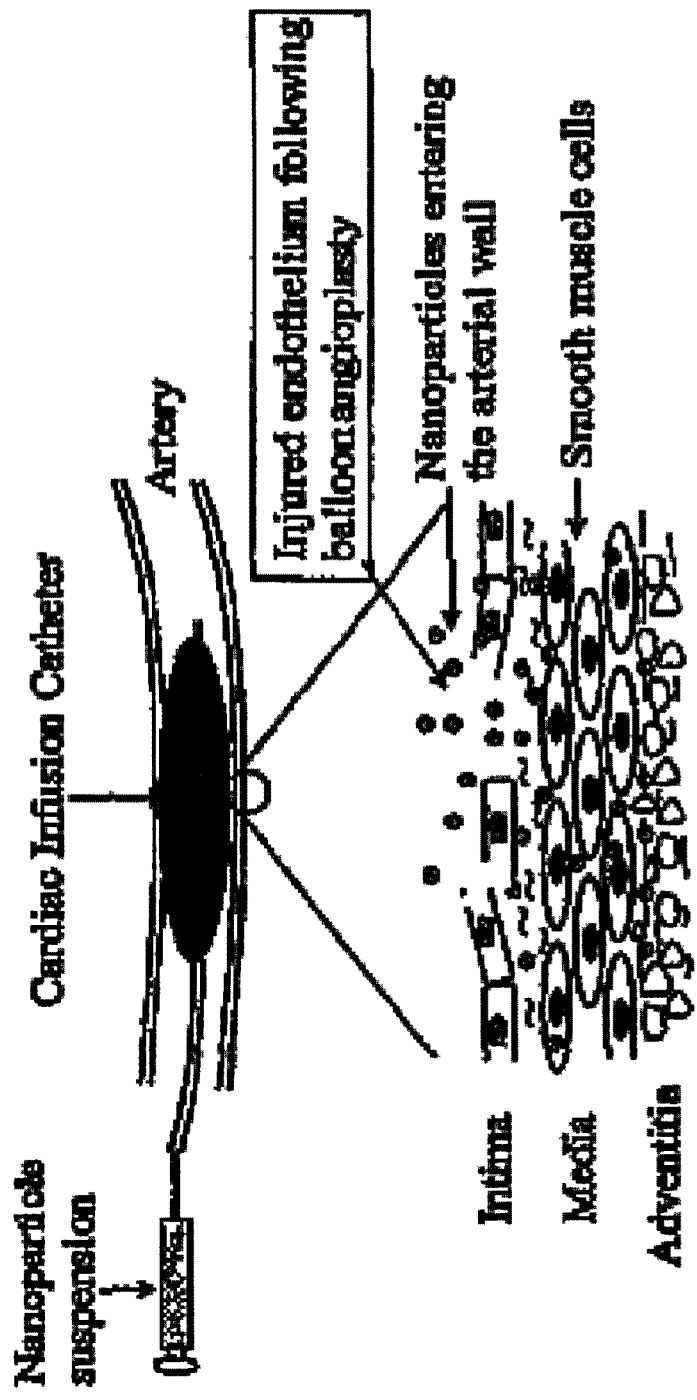
FIG. 1 is a schematic diagram depicting the localization of nanoparticles in the arterial wall.

Although gene and drug therapy approaches have been extensively investigated for the inhibition of restenosis, there are no efforts to investigate protein therapy for this purpose. This could be due to a multitude of factors including (1) poor stability of proteins in the biological environment, (2) non-availability of a suitable carrier system that could deliver the protein effectively to a specific intracellular target, and (3) inability to maintain a therapeutic protein level in the target cells/tissue for the duration required to inhibit restenosis.

Nanoparticle formulations have been investigated that can release the encapsulated protein in active form over a period of time. The main therapeutic strategy to prevent post-angioplasty restenosis has been to inhibit hyperplasia that is primarily caused by the migration and proliferation of vascular smooth muscle cells (VSMCs) and achieve vascular repair as indicated by re-endothelialization of the injured artery. Hyperplasia leads to re-obstruction of the injured artery in 30 to 50% patients undergoing balloon angioplasty. Over 1.5 million such procedures are performed annually worldwide, and in the US alone, 14 million people suffer from coronary artery disease, of which approximately 1 million undergo angioplasty annually. It is estimated that clinically significant restenosis continues to occur in >14% of elderly patients within the first year of undergoing coronary intervention procedure. This adds on average, $2747 per patient to the annual cost of follow-up care after angioplasty. Therefore, there are significant efforts to reduce the incidence of restenosis.

The essential aim of the invention is to inhibit restenosis by delivering a protein in a target blood vessel (e.g., artery or vein) that can inhibit the proliferation of VSMCs by the induction of cell cycle arrest (i.e., cellular senescence), and in some cases, the induction of apoptosis. The sustained release properties of nanoparticle formulations can maintain the low level of protein that maintains the cell-cycle arrest phase until the time that vascular repair occurs (i.e., re-endothelialization). Efforts are underway to develop cell/tissue specific, efficient, and safer gene expression vectors which can be used for arterial gene delivery to inhibit restenosis (1). However, the efficacy of gene therapy may be limited because it is not known how gene transfection occurs in the diseased cells. It is known that a significant number of VSMCs undergo apoptosis (in humans—20 to 30%, in rat carotid model—60 to 70%) in the injured artery within hours following angioplasty. In addition to the loss of cells that occurred due to angioplasty and apoptosis, a further loss of VSMCs due to cytotoxic drugs could lead to significant elastic recoiling of the artery. This results in a reduced lumen diameter, collapse of the artery or aneurysm causing arterial rupture, and bleeding. Moreover, greater loss of VSMCs provokes a greater body response to the injury (e.g. accumulation of platelets and secretion of growth factors) resulting in greater hyperplasia.

A better alternative to gene and drug therapy approaches could be a protein therapy, whereby a therapeutic protein is delivered to the target tissue or cells as shown, for example, in FIG. 1. With an effective delivery mechanism, one would be able to modulate more precisely the dose and the duration of protein delivery in the target artery to achieve inhibition of restenosis. Without being bound by theory, p53 plays central role in the control of cell growth and proliferation, and perhaps stabilizes VSMCs from undergoing apoptosis, thus, p53 can prevent the further cascade of events including inflammatory response that leads to hyperplasia. The fact that p53 levels are down regulated in the injured artery immediately following angioplasty and remain low during the proliferative phase of hyperplasia (10-14 days) provides a compelling evidence of its role in development of hyperplasia (2). Although p53 is known to affect the cell-cycle, as well as inducing apoptosis, its effect also depends on the level of gene expression and cell type. At a lower level of gene expression, p53 can inhibit cell proliferation primarily by cell-cycle arrest in G1 phase, whereas at higher levels, p53 can induce cell apoptosis (3,4).

p53 in Restenosis

The transcription factor, p53 regulates cell proliferation by multiple mechanisms including increase in cell surface expression of the death ligand receptor Fas (5-8), or activation of apoptotic genes such as Bax (9), or cell-cycle arrest through the cyclin dependent kinase inhibitor p21 (10,11). The p53 protein acts as a checkpoint in the cell cycle, either preventing or initiating programmed cell death (apoptosis). p53 also switches on a series of protective genes when the cell is exposed to stressful events.

Inhibition of VSMC proliferation has been demonstrated with wt-p53 gene using hemagglutinating virus of Japan (HVJ) liposome complex (12), and adenoviral vector (13) in animal models. Recent studies have shown that p53 deficiency promotes atherogenesis in murine models in which atherosclerosis was induced by remnant-like lipoproteins with absence or dysfunctional apoE (11), which suggests a role of p53 in vascular proliferative response (14). p53 protein could also protect VSMCs from stress-induced apoptosis (from exposure to growth factors) following angioplasty because of its protective effect on cell genome (15). Therefore, with protein therapy, there could be reduced vascular recoiling, and the long-term patency of the artery will not be a concern. The efficacy of the approach would depend on achieving sustained protein transfection in the target artery that would inhibit the proliferation of VSMCs primarily by cell-cycle arrest. Thus, sustained release NPs could be more effective in our studies than other systems (e.g, lipid complexes) which show relatively higher but transient protein transfection.

p53 Protein vs. Gene Delivery

Using protein therapy, it should be possible to modulate the dose and duration of p53 effect in the target blood vessel (e.g., artery or vein) depending on the therapeutic response measured by inhibition of restenosis. This can be achieved by readjusting the NP formulation parameters for protein loading and its release profile. An exemplary formulation described herein contains only 0.4 pg protein per mg NPs (0.04% w/w loading). Notably, it is possible to load as much as 10,000 pg protein per mg NPs (10% w/w loading). Similarly, one can change the protein release rate and duration of release by selecting suitable polymer composition (lactide to glycolide ratio), and molecular weight in the formulation of NPs. Since p53 protein is more potent, the dose of NPs required in the target artery would be significantly lower than that would be required for a less potent drug such as dexamethasone. The lower dose of NPs would increase the efficiency of uptake of NPs by the target artery, and would reduce the down-stream flow of excess of NPs, hence, the protein therapy could be more "target specific".

In previous studies using a porcine model, it was demonstrated that an increase in the arterial uptake of NPs with an increase in the dose of NPs infused was marginal beyond a certain dose, and the excess of the administered dose flows downstream (16). Potency of therapeutic agent is critical to developing an effective and target-specific NP-based system (or any other colloidal drug delivery system) for the inhibition of restenosis. Considering that the target artery has a limited holding capacity for NPs, it is necessary that the desired therapeutic dose of drug is delivered in the target artery in the dose of NPs that can be localized in the artery. This can be achieved using p53 protein because of its potency.

Furthermore, it is necessary that a therapeutic dose of protein is maintained in the target artery in order to prevent the proliferation of VSMCs for a period of time that would allow the injured artery to undergo the repair process.

As one of skill in the art will appreciate, a nanoparticle in accordance with the methods and compositions of the present invention can be composed of a variety of injectable biodegradable polymers. Nanoparticles are said to be biodegradable if the polymer of the nanoparticle dissolves or degrades within a period that is acceptable in the desired application (usually in vivo therapy), usually less than five years, and desirably less than one year, upon exposure to a physiological solution of pH 6-8 having a temperature of between 25° C. and 37° C. As such, a nanoparticle for use in accordance with the methods and compositions of the present invention can be composed of homopolymers or copolymers prepared from monomers of polymers disclosed herein, wherein the copolymer can be of diblock, triblock, or multiblock structure as described in U.S. Patent Application 20060067925. Suitable polymers include, but are not limited to, poly(lactide-co-glycolides), poly(lactic acid), poly(alkylene glycol), polybutylcyanoacrylate, poly(methylmethacrylate-co-methacrylic acid), poly-allylamine, polyanhydride, polyhydroxybutyric acid, or polyorthoesters and the like. In particular embodiments, a nanoparticle is composed of a copolymer of a poly (lactic acid) and a poly(lactide-co-glycolide). Particular combinations and ratios of polymers are well-known to the skilled artisan and any suitable combination can be used in the nanoparticle formulations of the present invention. Generally, the resulting nanoparticle typically ranges in size from between 1 nm and 1000 nm, or more desirably between 1 nm and 100 nm.

A nanoparticle of the present invention can further contain a polymer that affects the charge or lipophilicity or hydrophilicity of the particle. Any biocompatible hydrophilic polymer can be used for this purpose, including but not limited to, poly(vinyl alcohol).

To further enhance delivery of a therapeutically effective amount of an active agent, a nanoparticle of the present invention can further contain a targeting moiety (e.g., a protein transduction domain). As used herein, a targeting moiety is any molecule which can be operably attached to a nanoparticle of the present invention to facilitate, enhance, or increase the transport of the nanoparticle into target tissue. Such a moiety can be a protein, peptide or small molecule. For example, a variety of protein transduction domains, including the HIV-1 Tat transcription factor, Drosophila Antennapedia transcription factor, as well as the herpes simplex virus VP22 protein have been shown to facilitate transport of proteins into the cell (Wadia and Dowdy, (2002) Curr. Opin. Biotechnol. 13:52-56). Further, an arginine-rich peptide (Futaki, (2002) Int. J. Pharm. 245:1-7), a polylysine peptide containing Tat PTD (Hashida et al., (2004) Br. J. Cancer 90(6):1252-8); Deshayes et al., (2004) Biochemistry 43(6):1449-57) or an HSP70 protein or fragment thereof (WO 00/31113) is suitable for targeting a nanoparticle of the present invention. Not to be bound by theory, it is believed that such transport domains are highly basic and appear to interact strongly with the plasma membrane and subsequently enter cells via endocytosis (Wadia et al., (2004) Nat. Med. 10:310-315). Animal model studies indicate that chimeric proteins containing a protein transduction domain fused to a full-length protein or inhibitory peptide can protect against ischemic brain injury and neuronal apoptosis; attenuate hypertension; prevent acute inflammatory responses; and regulate long-term spatial memory responses (Blum and Dash, (2004) Learn. Mem. 11:239-243; May et al., (2000) Science 289:1550-1554; Rey et al., (2001) Circ. Res. 89:408-414; Denicourt and Dowdy, (2003) Trends Pharmacol. Sci. 24:216-218).

To conjugate or operably attach the targeting moiety to a nanoparticle of the present invention, standard methods, such as the epoxy activation method can be employed. The nanoparticle surface is contacted with an epoxy compound (e.g., DENACOL®, Nagase America Co., CAl which reacts with the hydroxyl functional group of, e.g., the Polyvinyl Alcohol (PVA) associated with the nanoparticle surface. The epoxy activation of the nanoparticle creates multiple sites for reaction with a ligand and also serves as a linkage between the nanoparticle surface and the peptide to avoid steric hindrance for interaction of the peptide with the cell membrane (Labhasetwar et al., (1998) J. Pharm. Sci. 87:1229-34). The epoxy groups can react with many functional groups including amine, hydroxyl, carboxyl, aldehyde, and amide under suitable pH and buffer conditions; therefore increasing the number of possible targeting moieties which can be employed.

A nanoparticle formulation of the present invention can further contain a plasticizer to facilitate sustained release of the encapsulated active agent by maintaining the structure of the nanoparticle. Release of molecules (e.g., proteins, DNA or oligonucleotides) from nanoparticles formulated from block copolymers is, in general, not continuous. Typically, there is an initial release followed by a very slow and insignificant release thereafter. Not to be bound by theory, it is contemplated that the release profile may be as a result of the rapid initial drop in the molecular weight of the polymer which reduces the glass transition temperature of the polymer to below body temperature (37° C.); the glass transition temperature of copolymers prior to release is above body temperature (~45 to 47° C.). Moreover, with degradation, these polymers become softer thereby closing the pores which are created during the initial release phase (due to the release of active agent from the surface). Therefore, an inert plasticizer is added to a nanoparticle formulation disclosed herein to maintain the glass transition temperature above 37° C. despite a decline in molecular weight of the polymer with time. In this manner, the pores remain open and facilitate a continuous release of the encapsulated active agent. Suitable plasticizers are generally inert and can be food/medical grade or non-toxic plasticizers including, but not limited to, triethyl citrate (e.g., CITROFLEX®, Morflex Inc., Greensboro, N.C.), glyceryl triacetate (e.g., Triacetin, Eastman Chemical Company, Kingsport, Tenn.), L-tartaric acid dimethyl ester (i.e., dimethyl tartrate, DMT) and the like. A particularly suitable plasticizer is L-tartaric acid dimethyl ester.

The amount of plasticizer employed in a nanoparticle composition can range from about 5% to 40% weight of the nanoparticle, more desirably from about 5% to 20% weight of the nanoparticle. In particular embodiments, the plasticizer encompasses about 10 weight percent of the nanoparticle composition.

By enhancing the release profile of an active agent, a plasticizer-containing nanoparticle has utility in the delivery of a variety of active agents to a variety of tissues or organs. Accordingly, the present invention further relates to a composition for sustained or continuous release of an effective amount of an active agent, for example p53 protein or shorter active fragments of p53 protein, wherein said composition contains an active agent, at least one biodegradable polymer, and an inert plasticizer. As used herein, "controlled release", "sustained release", and similar terms are used to denote a mode of active agent delivery that occurs when the active agent is released from the nanoparticle formulation at an ascertainable and controllable rate over a period of time, rather than dispersed immediately upon application or injection. Controlled or sustained release can extend for hours, days or months, and can vary as a function of numerous factors. For the composition of the present invention, the rate of release will depend on the type of the plasticizer selected and the concentration of the plasticizer in the composition. Another determinant of the rate of release is the rate of hydrolysis of the linkages between and within the polymers of the nanoparticle. Other factors determining the rate of release of an active agent from the present composition include particle size, acidity of the medium (either internal or external to the matrix) and physical and chemical properties of the active agent in the matrix.

As will be appreciated by the skilled artisan, the nanoparticle compositions of the present invention can further contain additional fillers, excipients, binders and the like depending on, for example, the route of administration and the active agent used. A generally recognized compendium of such ingredients and methods for using the same is Remington: The Science and Practice of Pharmacy, Alfonso R. Gennaro, editor, 20th ed. Lippingcott Williams & Wilkins: Philadelphia, Pa., 2000.

Definitions

The following definitions are provided to facilitate an understanding of the present invention:

The terms "p53", "p53 protein", or "p53 protein fragment" all refers to the nuclear protein that plays an essential role in the regulation of cell cycle, specifically in the transition from G0 to G1. p53 is a DNA-binding protein containing DNA-binding, oligomerization and transcription activation domains. It is postulated to bind as a tetramer to a p53-binding site and activate expression of downstream genes that inhibit growth and/or invasion, and thus function as a tumor suppressor. Mutants of p53 that frequently occur in a number of different human cancers fail to bind the consensus DNA binding site, and hence cause the loss of tumor suppressor activity. Exemplary "p53" proteins include the human p53, such as that listed by GenBank protein ID: NP_000537, and its structural and functional polymorphisms. A list of p53 protein fragments for use in the NP formulations are listed in Table I. It has been suggested that p53 fragments lacking N- and/or C-terminal parts could have an effect on the regulation of p53 stability or function. The decoy p53 fragments can indirectly influence the function of p53. For example, it has been shown that mdm2 can promote the destabilization of p53 and that this function depends on interaction of both proteins. p53 decoy fragments can bind to mdm2 which can then make available the transcriptionally active p53. This could enhance the pro-apoptotic function of p53 in cancer treatment or its protective effect in normal cells from oxidative stress or radiation induced DNA damage (Kubbutal and Vousden, Molecular Medicine Today, June 1998, pgs. 250-256).

These non-functional p53 fragments discussed above may lack any known biological activity and can act as decoy molecules in the cell rather than inducing apoptosis or senescence. For example, the decoy p53 fragments could be delivered to suppress the activity of any mutated p53 protein, if present in the cell. Alternatively, the decoy fragments can be delivered to act as binding partners or substrates in the cell, thereby allowing wild type p53 to function normally in a particular cellular context.

As used herein, a "peptide", "protein", and "polypeptide" are used interchangeably and refer to a compound made up of a chain of amino acid residues linked by peptide bonds. The sequence for peptides is given in the order from the amino terminus to the carboxyl terminus. A peptide or peptide fragment is "derived from" a parent peptide or polypeptide if it has the amino acid sequence that is identical or homologous to the amino acid sequence of the parent peptide or polypeptide.

The term "isolated protein" or "isolated and purified protein" is sometimes used herein. This term refers primarily to a p53 protein of the invention, for example, those found in Table I. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "nanoparticle" refers to a particle having a size measured on the nanometer scale. As used herein, the "nanoparticle" refers to a particle having a matrix-type structure with a size of less than about 1,000 nanometers. When the nanoparticle includes a bioactive component, the bioactive component is entangled or embedded in the matrix-type structure of the nanoparticle. Nanoparticles include particles capable of containing a therapeutic/diagnostic agent that is to be released within a mammalian body, including specialized forms such as nanospheres, whether natural or artificial.

A "therapeutic agent" as used herein refers to an agent which can mitigate, cure, treat or prevent a disease or condition. It is particularly desirable that the therapeutic agent be capable of exerting it effect locally (i.e., at or near the site of the disease or condition). Exemplary therapeutic agents include, but are not limited to, antibiotics, anti-restenotics, anti-proliferative agents, anti-neoplastic agents, chemotherapeutic agents, cardiovascular agents, anti-inflammatory agents, immunosuppressive agents, anti-apoptotic and anti-tissue damage agents.

The term "delivery" as used herein refers to the introduction of foreign molecule (i.e., protein containing nanoparticle) in cells.

The phrase "blood vessel" refers to components of the circulatory system which functions to move blood throughout the body. This phrase includes both arteries, which move blood away from the heart, and veins, which circulate blood back to the heart.

The term "treating" as used herein means the prevention, reduction, partial or complete alleviation or cure of a disease.

The term "administration" as used herein means the introduction of a foreign molecule (i.e., protein containing nanoparticle) into a cell. The term is intended to be synonymous with the term "delivery". Administration also refers to the methods of delivery of the compounds of the invention (e.g., routes of administration such as, without limitation, intravenous, intra-arterial, intramuscular, subcutaneous, intrasynovial, infusion, sublingual, transdermal, oral, or topical). The preferred method of delivery is to the blood vessel (e.g., artery or vein) or in particular applications to the carotid, coronary, femoral, renal, or cerebral artery, depending on the site of injury.

As used herein, an "effective amount" of the p53 protein or protein fragment is an amount sufficient to cause cell cycle arrest, or an amount sufficient to inhibit cell proliferation in a subject.

An "individual" as used herein refers to any vertebrate animal, preferably a mammal, and more preferably a human.

As used herein, "proliferating" and "proliferation" refer to cells undergoing mitosis. Throughout this application, the term "proliferative disorder" refers to any disease/disorder marked by unwanted or aberrant proliferation of tissue. As used herein, the term "cell proliferative disorder" refers to conditions in which the unregulated and/or abnormal growth of cells can lead to the development of an unwanted condition or disease, which can be cancerous or non-cancerous, for example a psoriatic condition.

The term "restenosis" refers to any pre-occlusive lesion that develops following a reconstructive interventional procedure such as balloon angioplasty or stenting in a diseased blood vessel. The term is not only applied to the recurrence of a pre-existing stenosis, but also to previously normal vessels such as vein grafts that become partially occluded following vascular bypass. Restenosis refers to any luminal narrowing that occurs following an injury to the vessel wall. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis. Restenosis typically results from a hyperplasia. The loss of endothelium exposes the smooth muscle cells to growth factors, causing them to migrate and proliferate into the lumen of the artery. Restenosis is believed to occur in about 30% to 60% of lesions treated by angioplasty and about 20% of lesions treated with stents within 3 to 6 months following the procedure.

The term "inflammation" as used herein refers to the biologic response of body tissue to injury, irritation, or disease which can be caused by harmful stimuli, for example, pathogens, damaged cells, or irritants. Inflammation is typically characterized by pain and swelling. Inflammation is intended to encompass both acute responses, in which inflammatory processes are active (e.g., neutrophils and leukocytes), and chronic responses, which are marked by slow progress, a shift in the type of cell present at the site of inflammation, and the formation of connective tissue. The term "inflammation" also refers to "VSMC inflammation" in a patient following angioplasty.

Pharmaceutical Compositions

Methods of the invention directed to treating restenosis involve the administration of p53 protein containing nanoparticles. One skilled in the art appreciates that a p53 protein containing nanoparticle can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption, and most preferably, by injection.

Administration of the pharmaceutical preparation is preferably in an "effective amount" this being sufficient to show benefit to the individual. This amount prevents, alleviates, abates, or otherwise reduces the severity of symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the patient and the desired effect. Appropriate concentrations for alleviation of a particular pathological condition may be determined by dosage concentration curve calculations, as known in the art.

Nanoparticle compositions provided herein can be prepared for local administration by a variety of different routes, including for example, directly to site of the disease or condition (e.g., a site of injury or tumor) under direct vision (e.g., at the time of surgery or via endoscopic procedures) or via percutaneous drug delivery to the exterior (adventitial) surface of the site of the disease or condition (e.g., perivascular delivery). As an alternative, the placement of nanoparticles via a catheter can also be accomplished.

Perivascular drug delivery involves percutaneous administration of the nanoparticle composition using a needle or catheter directed via ultrasound, computed tomography, fluoroscopic, positron emission tomography, magnetic resonance imaging or endoscopic guidance to the site of the disease or condition. Alternatively, the procedure can be performed intra-operatively under direct vision or with additional imaging guidance. In the case of restenosis or other cardiovascular diseases, such a procedure can also be performed in conjunction with endovascular procedures such as angioplasty, atherectomy, or stenting or in association with an operative arterial procedure such as endarterectomy, vessel or graft repair or graft insertion.

For example, in a patient with narrowing of the superficial femoral artery, balloon angioplasty would be performed in the usual manner (i.e., passing a balloon angioplasty catheter down the artery over a guide wire and inflating the balloon across the lesion). Prior to, at the time of, or after angioplasty, a needle would be inserted through the skin under ultrasound, fluoroscopic, or CT guidance and a therapeutic agent (e.g., p53 protein in a sustained-release nanoparticle) would be infiltrated through the needle or catheter in a circumferential manner directly around the area of narrowing in the artery. This could be performed around any artery, vein or graft, but ideal candidates for this intervention include diseases of the carotid, coronary, iliac, common femoral, superficial femoral and popliteal arteries and at the site of graft anastomosis. Logical venous sites include infiltration around veins in which indwelling catheters are inserted.

Nanoparticle compositions of the present invention can be administered either alone, or in combination with a pharmaceutically or physiologically acceptable carrier, excipient or diluent. Generally, such carriers should be nontoxic to recipients at the dosages and concentrations employed. Ordinarily, the preparation of such compositions entails combining the nanoparticle composition of the present invention with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients.

Representative examples of restenosis therapeutic agents include, for example, anti-angiogenic agents such as anti-invasive factor (Eisentein et al., (1975) Am. J. Pathol. 81:337-346; Langer et al., (1976) Science 193:70-72; Horton et al., (1978) Science 199:1342-1345), retinoic acid and derivatives thereof which alter the metabolism of extracellular matrix components to inhibit angiogenesis, tissue inhibitor of metalloproteinase-1, tissue inhibitor of metalloproteinase-2, plasminogen activator inhibitor-1, plasminogen activator inhibitor-2, and anginex (Griffioen et al., (2001) Biochem. J. 354(Pt 2):233-42); collagen inhibitors such as halofuginone or batimistat; antisense oligonucleotides directed to nucleic acid sequences encoding c-myc or c-myb; growth factor inhibitors such as tranilast, trapidil or angiopeptin; antioxidants such as probucol, anti-thrombotics such as heparin or abciximab, anti-proliferative agents such as AG-1295 (Fishbein, et al. (2000) Arterioscler. Thromb. Vasc. Biol. 20:667), tyrphostin (Banai, et al. (2005) Biomaterials 26(4):451-61), pacitaxel or other taxanes (Scheller et al., (2004) Circulation 110(7):810-4), isoflavones (Kanellakis et al., (2004) Atherosclerosis 176(1):63-72), rapamycin or derivatives or analogs thereof (Schachner et al., (2004) Ann. Thorac. Surg. 77(5): 1580-5), vincristine, vinblastine, HMG-CoA reductase inhibitors, doxorubicin, colchicines, actinomycin D, mitomycin C, cyclosporine, or mycophenolic acid; anti-inflammatory agents such as dexamethasone (Liu et al. (2004) Expert Rev. Cardiovasc. Ther. 2(5):653-60), methylprednisolone, or gamma interferon; and the like which exhibits antirestenotic activity.

Other therapeutic agents that can be utilized in accordance with the present invention include anti-proliferative, anti-neoplastic or chemotherapeutic agents to prevent or treat tumors. Representative examples of such agents include androgen inhibitors; antiestrogens and hormones (e.g., flutamide, leuprolide, tamoxifen, estradiol, estramustine, megestrol, diethylstilbestrol, testolactone, goserelin, medroxyprogesterone); cytotoxic agents (e.g., altretamine, bleomycin, busulfan, carboplatin, carmustine (BiCNU), cisplantin, cladribine, dacarbazine, dactinomycin, daunorubicin, doxorubicin, estramustine, etoposide, lomustine, cyclophosphamide, cytarabine, hydroxyurea, idarubicin, interferon alpha-2a and -2b, ifosfamide, mitoxantrone, mitomycin, paclitaxel, streptozocin, teniposide, thiotepa, vinblastine, vincristine, vinorelbine); antimetabolites and antimitotic agents (e.g., floxuridine, 5-fluorouracil, fluarabine, interferon alpha-2a and -2b, leucovorin, mercaptopurine, methotrexate, mitotane, plicamycin, thioguanine, colchicines); folate antagonists and other anti-metabolites; vinca alkaloids; nitrosoureas; DNA alkylating agents; purine antagonists and analogs; pyrimidine antagonists and analogs; alkyl solfonates; enzymes (e.g., asparaginase, pegaspargase); and toxins (e.g., ricin, abrin, diphtheria toxin, cholera toxin, gelonin, pokeweed antiviral protein, tritin, Shigella toxin, and Pseudomonas exotoxin A).

Further therapeutic agents that can be utilized within the present invention include cardiovascular agents such as antihypertensive agents; adrenergic blockers and stimulators (e.g., doxazosin, guanadrel, guanethidine, pheoxybenzamine, terazosin, clonidine, guanabenz); alpha-/beta-adrenergic blockers (e.g., labetalol); angiotensin converting enzyme (ACE) inhibitors (e.g., benazepril, catopril, lisinopril, ramipril); ACE-receptor antagonists (e.g., losartan); beta blockers (e.g., acebutolol, atenolol, carteolol, pindolol, propanolol, penbatolol, nadolol); calcium channel blockers (e.g., amiloride, bepridil, nifedipine, verapamil, nimodipine); antiarrythmics, groups I-IV (e.g., bretylium, lidocaine, mexiletine, quinidine, propranolol, verapamil, diltiazem, trichlormethiazide, metoprolol tartrate, carteolol hydrochloride); and miscellaneous antiarrythmics and cardiotonics (e.g., adenosine, digoxin, caffeine, dopamine hydrochloride, digitalis).

Additional therapeutic agents that can be used in accord with the present invention include anti-inflammatory agents. Representative examples of such agents include nonsteroidal agents (NSAIDS) such as salicylates, diclofenac, diflunisal, flurbiprofen, ibuprofen, indomethacin, mefenamic acid, nabumetone, naproxen, piroxicam, ketoprofen, ketorolac, sulindac, tolmetin. Other anti-inflammatory drugs include steroidal agents such as beclomethasone, betamethasone, cortisone, dexamethasone, fluocinolone, flunisolide, hydorcortisone, prednisolone, and prednisone. Immunosuppressive agents are also contemplated (e.g., adenocorticosteroids, cyclosporin).

Therapeutic agents also include anti-tissue damage agents. Representative examples of such agents include superoxide dismutase; immune modulators (e.g., lymphokines, monokines, interferon α and β); and growth regulators (e.g., IL-2, tumor necrosis factor, epithelial growth factor, somatrem, fibronectin, GM-CSF, CSF, platelet-derived growth factor, somatotropin, rG-CSF, epidermal growth factor, IGF-1).

Figure 2:
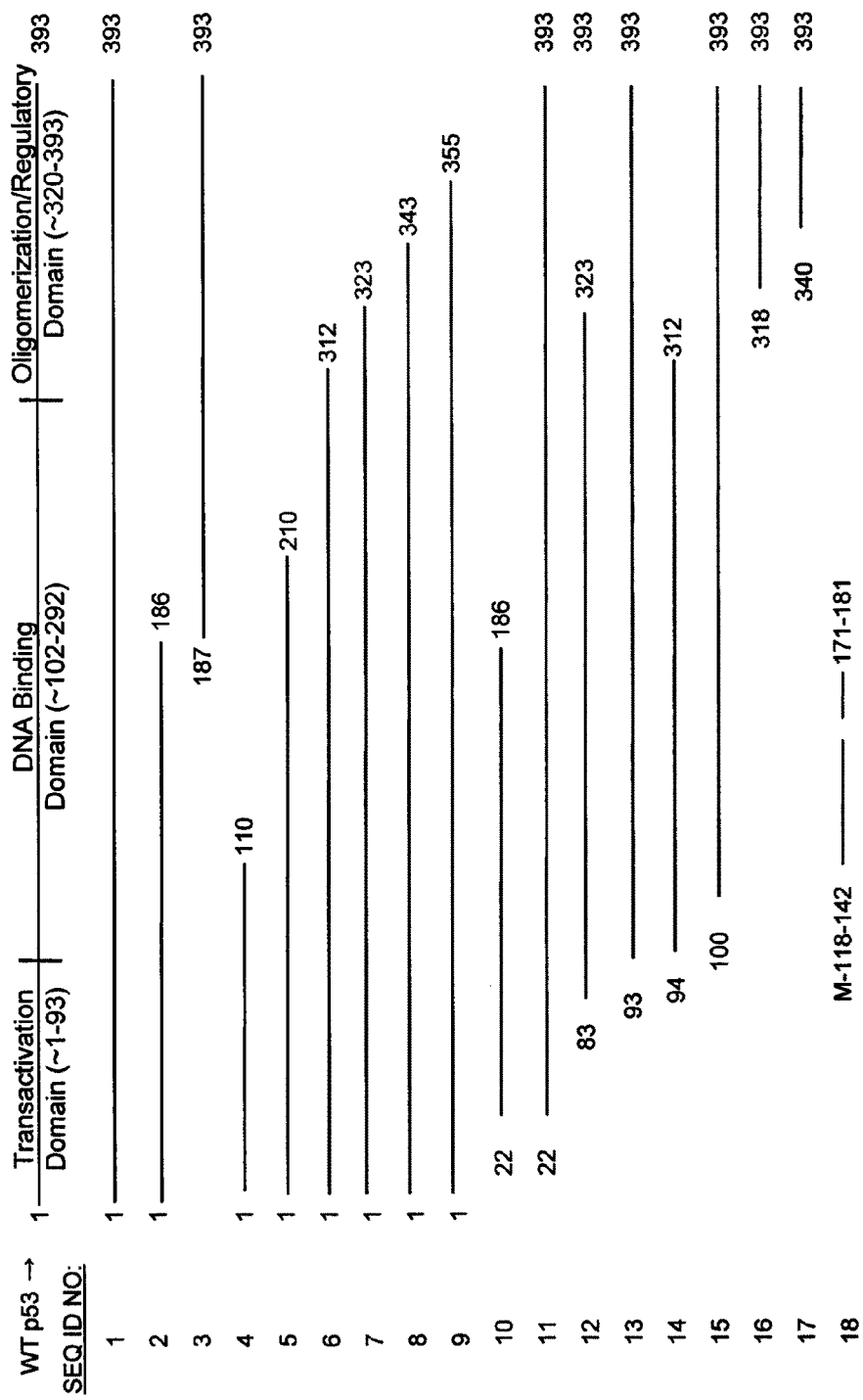
FIG. 2 shows the different domains of p53 and the p53 fragments described in Table I.

As mentioned previously, a preferred embodiment of the invention comprises delivery of p53 protein containing nanoparticles to a patient in need thereof. P53 protein sequences and fragments of p53 for use in the invention are provided in Table I and the different domains of the p53 protein fragments are shown schematically in FIG. 2. The sequences in Table I include several p53 protein fragments (SEQ ID NOs: 1-18). Additionally, the p53 related protein p63 and p73, as well as the cell cycle proteins p21 and p27 can be delivered in nanoparticle formulations, and the sequences in Table II represent protein and protein fragments useful for the present invention.

TABLE I p53 (GenBank Accession number: NP_000537)
protein sequences for use in nanoparticle formulations

| SEQ ID NO | Description | Reference | Biological Activity |
|---|---|---|---|
| 1 | Full-length (1-393 aa) | NP_000537 | Induces apoptosis/senescence |
| 2 | 1-186 aa | JBC (2006) 281:13566-13573 | Destabilizes mitochondria membrane/transcriptionally inactive (bax) |
| 3 | 187-393 aa | JBC (2006) 281:13566-13573 | Non-functional |
| 4 | 1-110 aa | JCI (2007) 117:1008-1018 | Non-functional |
| 5 | 1-210 aa | JCI (2007) 117:1008-1018 | Induces apoptosis via p73 |
| 6 | 1-312 aa | JMB (2002) 322:917-927 | Binds DNA |
| 7 | 1-323 aa | MCB (1994) 14:5182-5191 | Suppresses ras transformation |
| 8 | 1-343 aa | PNAS (1994) 91:1998-2002 | No transcriptional repression/low growth suppression |
| 9 | 1-355 aa | Gene Dev. (1998) 12:2831-2841 | Reduced acetylation |
| 10 | 22-186 aa | JBC (2006) 281:13566-13573 | Destabilizes mitochondria membrane |
| 11 | 22-393 aa | JBC (2006) 281:13566-13573 | Destabilizes mitochondria membrane/weak transcriptional activity (bax) |
| 12 | 83-393 aa | MCB (1994) 14:5182-5191 | No effect on ras transformation |
| 13 | 93-393 aa | JMB (2002) 322:917-927 | Binds DNA |
| 14 | 94-312 aa | JMB (2002) 322:917-927 | Binds DNA/thermodynamically stable |
| 15 | 100-393 aa | PNAS (1994) 91:1998-2002 | Represses transcription/low growth suppression |
| 16 | 318-393 aa | Gene Dev. (1998) 12:2831-2841 | Fully acetylated |
| 17 | 340-393 aa | MCB (1994) 14:5182-5191 | No effect on ras transformation |
| 18 | 37-aa fragment Met + 118-142 + 171-181 | JCI (2007) 117:1008-1018 | Induces apoptosis via p73/binds to iASPP |

TABLE II p21 (GenBank Accession number NP_000380),
p27 (GenBank Accession number NP_004055),
p63 (GenBank Accession number NP_003713),
and p73 (GenBank Accession number NP_005418)
protein sequences for use in nanoparticle formulations

| SEQ ID NO | Description | Reference |
|---|---|---|
| 19 | p21 (Full-length) 1-164 aa | NP_000380 |
| 20 | p21: (1-78 aa) | US Appl. 2005/0032038 |
| 21 | p21: (72-164 aa) | US Appl. 2005/0032038 |
| 22 | p27 (Full-length) 1-198 aa | NP_004055 |
| 23 | p27: (1-101 aa) | US Appl. 2005/0032038 |
| 24 | p27: (95-198 aa) | US Appl. 2005/0032038 |
| 25 | p73 (Full-length) 1-636 aa | NP_005418 |
| 26 | p73: 1-319 aa | BBRC (2005), 333(3):954-960 |
| 27 | p73: 319-636 aa | BBRC (2005), 333(3):954-960 |
| 28 | p63 (Full-length) 1-680 | NP_003713 |

The materials and method set forth below are provided to facilitate the practice of the present invention.

Formulation and Characterization of Nanoparticles

PLGA (27 mg; 50:50, inherent viscosity 1.31; LACTEL, formerly Birmingham Polymers, Inc., Birmingham, Ala.) was dissolved in 1 mL of chloroform. Dimethyl tartrate (DMT or tartaric acid dimethyl ester; density 1.238 g/mL; Sigma, St. Louis, Mo.) 3 mg was dissolved in the polymer solution. Protein (10 mg of rat serum albumin (SIGMA A6272) and 20 µg of p53 protein (BD Pharmingen #556439)) was dissolved in 300 µL of water. The protein solution was emulsified into the PLGA solution by vortexing for 1 minute and then sonicating for 2 minutes at 55 Watts energy output using a probe sonicator (XL 2015 Sonicator® ultrasonic processor, Misonix, Inc., Farmingdale, N.Y.).

The resulting primary emulsion was further emulsified into 12 mL of 2% PVA solution (PVA average molecular weight 30,000-70,000) by vortexing followed by sonicating for 2 minutes at 55 Watts. PVA solution was filtered through a 0.22 micron syringe filter and saturated with chloroform prior to use. A few drops of chloroform were added at a time into the PVA solution, shaken and the supernatant was used for the formulation.

The emulsion was stirred overnight on a stir plate at room temperature followed by desiccation under vacuum for 1 hour. Nanoparticles thus formed were separated by centrifugation at 30,000 rpm for 30 minutes at 4° C. (Beckman OPTIMA® LE-80K, Beckman Instruments, Inc., Palo Alto, Calif.). Pelleted nanoparticles were resuspended in water and centrifuged again as indicated above. The supernatant was collected and the process was repeated one additional time to remove unencapsulated protein and emulsifier. The supernatants were collected and analyzed for protein levels to determine the amount of protein not encapsulated in the nanoparticles. Protein levels were determined using BIORAD® assay kit.

Nanoparticles were suspended in water by sonication as above. The suspension was lyophilized for 48 hours (VirTis Company, Inc. freeze dryer, Gardiner, N.Y.).

The diameter of the nanoparticles was obtained with photon correlation spectroscopy (PCS) using quasi elastic light scattering equipment (ZETAPLUS®, zeta potential analyzer, Brookhaven Instruments Corp., Holtsville, N.Y.) and ZETAPLUS® particle sizing software (version 2.07).

The following examples are provided to illustrate certain embodiments of the invention. In particular, the experiments that follow were performed to assess release of p53 from the nanoparticle formulation described herein. These examples are not intended to limit the invention in any way.

Example I

Sustained Release of p53 Protein from Nanoparticles

Figure 3:
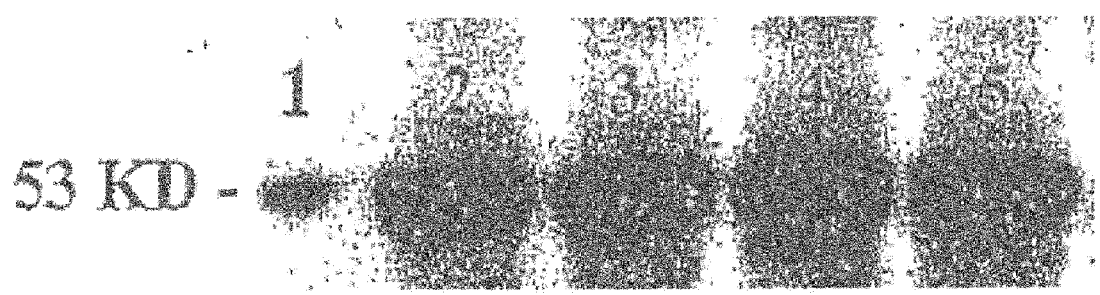
FIG. 3 is an SDS PAGE gel showing release of p53 from protein loaded NPs incubated in PBS in a double diffusion chamber. The receiver side of the buffer was withdrawn at different time intervals and analyzed. From left to right, Lane 1-200 ng of protein prior to entrapment in NPs; Lanes 2-5—p53 protein samples collected from the release study at day 1, day 3, day 7 and day 9 respectively.
Figure 4:
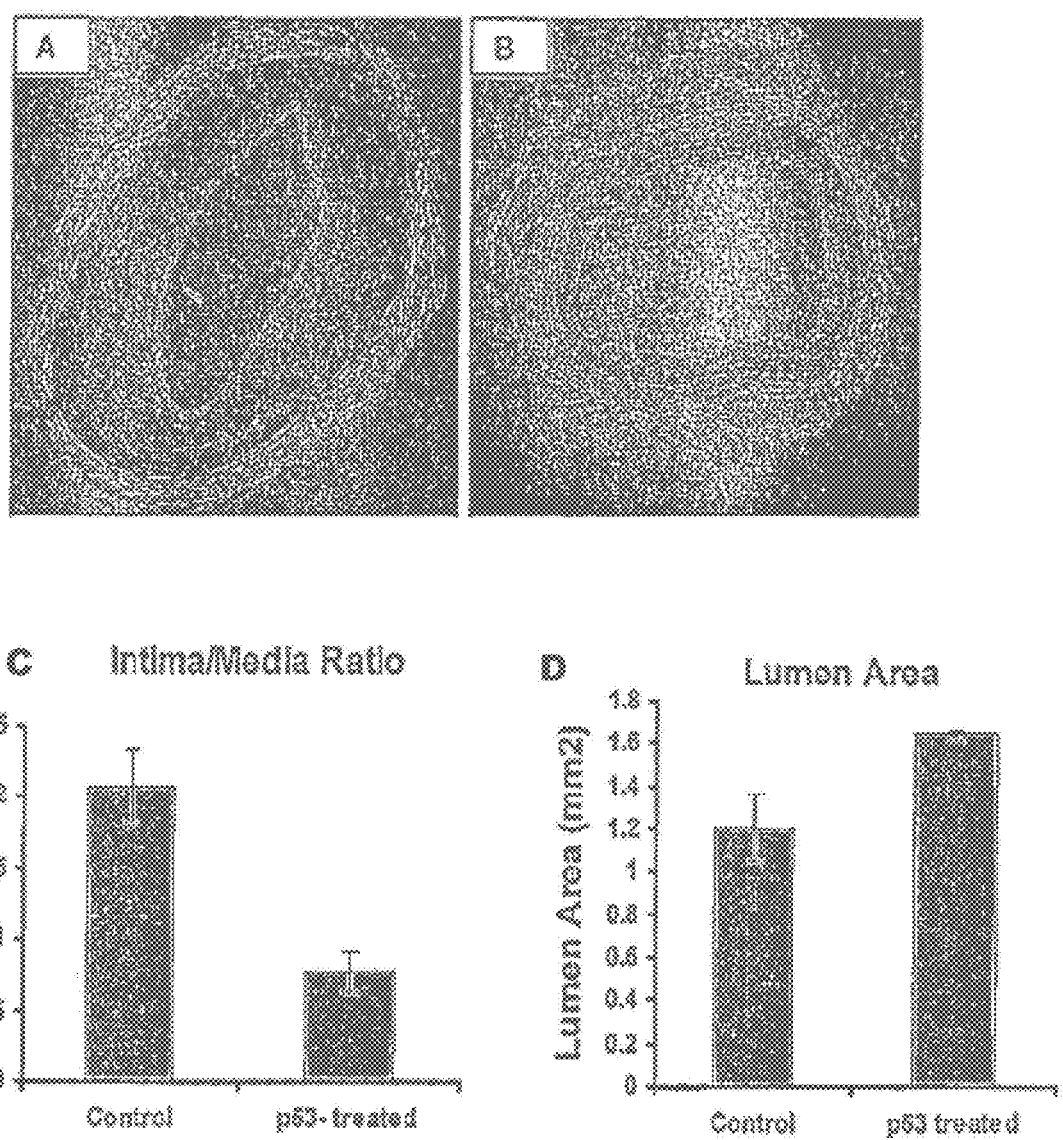
FIGS. 4, (A-D) are micrographs and graphs showing inhibition of restenosis with p53 protein therapy in a rat carotid artery model.

A western blot was performed to assess p53 release from the nanoparticle formulation (FIG. 3). The western blot analysis of p53 protein release from NPs demonstrated robust bands corresponding to the p53 protein band prior to its encapsulation. This confirms that the protein maintained its configuration following its encapsulating into the NPs, and also when it is released slowly from NPs.

Example II

Balloon Injury and Inhibition Restenosis with p53 Protein-Loaded NP in a Rat Carotid Artery Model The preliminary study in rat carotid artery model demonstrated significant inhibition of restenosis with single-dose localized administration of p53 protein-loaded NPs (dose of protein=1.6 microgram). After balloon injury, NP suspension in saline was infused over 5 minutes at 2 atm of pressure (three 1-min periods between infusions of 70 µl of the suspension, with a 1 min period between infusions). The control group contained NPs without p53 protein. After three weeks, infused arteries were isolated, sectioned every 3 mm from the proximal to the distal ends, and were analyzed for proliferation. See FIGS. 4A-4D. The data demonstrate that p53 protein in modified NPs is effective in inhibiting restenosis. There is significant inhibition of intima to media ratio (65% inhibition of restenosis), and a corresponding increase in the lumen diameter in the p53 protein treated animals as compared to that in control. In these experiments, protein alone in solution was clearly not as effective as that delivered in a nanoparticle formulation.

REFERENCES

1. P. Libby, Gene therapy of restenosis: promise and perils, Circ Res 82 (1998) 404-6.
2. D. W. Muller, The role of proto-oncogenes in coronary restenosis, Prog Cardiovasc Dis 40 (1997) 117-28.
3. K. Itahana, G. P. Dimri, E. Hara, Y. Itahana, Y. Zou, P. Y. Desprez, and J. Campisi, A role for p53 in maintaining and establishing the quiescence growth arrest in human cells, J Biol Chem 277 (2002) 18206-14.
4. L. Dubrez, J. L. Coil, A. Hurbin, F. de Fraipont, S. Lantejoul, and M. C. Favrot, Cell cycle arrest is sufficient for p53-mediated tumor regression, Gene Ther 8 (2001) 1705-12.
5. M. Bennett, K. Macdonald, S. W. Chan, J. P. Luzio, R. Simari, and P. Weissberg, Cell surface trafficking of Fas: a rapid mechanism of p53-mediated apoptosis, Science 282 (1998) 290-3.
6. H. Matsushita. R. Morishita, Aoki M. Tomita. Y. Taniyama. H. Nakagami, T. Shimozato. J. Higaki. Y. Kaneda, and T. Ogihara, Transfection of antisense p53 tumor suppressor gene oligodeoxynucleotides into rat carotid artery results in abnormal growth of vascular smooth muscle cells. Circulation 101 (2000) 1447-52.
7. D. Lin, M. T. Shields, S. J. Ullrich, E. Appella, and W. E. Mercer, Growth arrest induced by wild-type p53 protein blocks cells prior to or near the restriction point in late GI phase, Proc Natl Acad Sci 89 (1992) 9210-4.
8. K. Tanaka, J. P. Zou, K. Takeda, V. J. Ferrans, G. R. Sandford, T. M. Johnson, T. Finkel, and S. E. Epstein, Effects of human cytomegalovirus immediate-early proteins on p53-mediated apoptosis in coronary artery smooth muscle cells, Circulation 99 (1999) 1656-9.
9. C. Ihling, J. Haendeler, G. Menzel, R. D. Hess, G. Fraednch, H. E. Schaefer, and A. M. Zeiher, Coexpression of p53 and MDM2 in human atherosclerosis: implications for the regulation of cellularity of atherosclerotic lesions. J Pathol 185 (1998) 303-12.
10. W. S. el Deiry, T. Tokino, V. E. Velculescu, D. B. Levy, R. Parsons, J. M. Trent, D. Lin, W. E. Mercer, K. W. Kinzler, and B. Vogelstein, WAFI, a potential mediator of p53 tumor suppression, Cell 75 (1993) 817-25.
11. N. V. Guevara, H. S. Kim, E. I. Antonova, and L. Chan, The absence of p53 accelerates atherosclerosis by increasing cell proliferation in vivo, Nat Med 5 (1999) 335-9.
12. Y. Yonemitsu, Y. Kaneda, S. Tanaka, Y. Nakashima, K. Komori, K. Sugimachi, and K. Sueishi, Transfer of wild-type p53 gene effectively inhibits vascular smooth muscle cell proliferation in vitro and in vivo, Circ. Res 82 (1998) 147-56.
13. M. Scheinman, E. Ascher, E. S. Levi, A. Hingorani, D. Shirazian, and P. Seth, p53 gene transfer to the injured rat carotid artery decreases neointimal formation, J Vasc Surg 29 (1999) 360-9.
14. M. Aoki, R. Morishita, H. Matsushita, S. Hayashi, H. Nakagami, K. Yamamoto, A. Moriguchi, Y. Kaneda, J. Higaki, and T. Ogihara, Inhibition of the p53 tumor suppressor gene results in growth of human aortic vascular smooth muscle cells. Potential role of p53 in regulation of vascular smooth muscle cell growth, Hypertension 34 (1999) 192-200.
15. A. Aranda Anzaldo, F. Orozco Velasco, E. Garcia Villa, and P. Gariglio, p53, is a rate-limiting factor in the repair of higher-order DNA structure, Biochim Biophys Acta 1446 (1999) 181-92.
16. V. Labhasetwar, C. Song, W. Humphrey, R. Shebuski, and R. J. Levy, Arterial uptake of biodegradable nanoparticles: effect of surface modifications, J Pharm Sci 87 (1998) 1229-34.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for inhibiting restenosis of a blood vessel comprising administering an effective amount of a nanoparticle formulation comprising p53 protein, at least one biodegradable polymer and an inert plasticizer, said nanoparticle formulation being administered via said blood vessel to a subject in need of treatment, thereby inhibiting restenosis in said blood vessel.

2. The method of claim 1, wherein said p53 protein is wild type p53 of SEQ ID NO: 1, wherein said p53 protein is effective to promote vascular repair.

3. The method of claim 1, wherein said biodegradable polymer comprises a poly(lactide-co-glycolide), poly(lactic acid), poly(alkylene glycol), polybutylcyanoacrylate, poly(methylmethacrylate-co-methacrylic acid), poly-allylamine, polyanhydride, polyhydroxybutyric acid, or a polyorthoester or a combination thereof.

4. The method of claim 1, wherein the nanoparticle further comprises a targeting moiety.

5. The method of claim 1, wherein said blood vessel is an artery and is selected from the group consisting of carotid, coronary, femoral, renal, and cerebral.

6. The method of claim 1, wherein the plasticizer comprises L-tartaric acid dimethyl ester, triethyl citrate, or glyceryl triacetate.

7. The method of claim 1, wherein said p53 protein is the sole agent administered to inhibit said restenosis.

8. A method of managing vascular inflammation in a patient following angioplasty comprising administering to said patient via a blood vessel, a nanoparticle formulation comprising a protein, at least one biodegradable polymer and an inert plasticizer, wherein said protein is selected from the group consisting of SEQ ID NO: 1, 2, 5-15 and 18 in a pharmaceutically acceptable carrier in an effective amount to manage vascular inflammation.

9. The method of claim 8, wherein said formulation inhibits restenosis following an angioplasty.

10. The method of claim 8, wherein said formulation promotes vascular repair.

11. A method for inhibiting restenosis of a blood vessel comprising administering an effective amount of a p53 protein of SEQ ID NO: 1 containing nanoparticle formulation for sustained release of an effective amount of p53 protein, said formulation comprising p53 protein, at least one bio-degradable polymer, and an inert plasticizer via said blood vessel to a subject in need of treatment, thereby inhibiting restenosis in said blood vessel.

12. A method of managing vascular inflammation in a patient following angioplasty comprising administering to said patient via a blood vessel, a p53 protein of SEQ ID NO:1 containing nanoparticle formulation for sustained release of p53 protein, said formulation comprising p53 protein, at least one bio-degradable polymer, and an inert plasticizer in an effective amount to manage vascular inflammation at the site of injury.

* * * * *

SEQUENCE LISTING

```
<160> NUMBER OF SEQ ID NOS: 28

<210> SEQ ID NO 1
<211> LENGTH: 393
<212> TYPE: PRT
<213> ORGANISM: Homo Sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220
```

```
Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
            290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 2
<211> LENGTH: 186
<212> TYPE: PRT
<213> ORGANISM: Homo Sapiens

<400> SEQUENCE: 2

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp
                180                 185

<210> SEQ ID NO 3
```

<211> LENGTH: 207
<212> TYPE: PRT
<213> ORGANISM: Homo Sapiens

<400> SEQUENCE: 3

Gly Leu Ala Pro Pro Gln His Leu Ile Arg Val Glu Gly Asn Leu Arg
1               5                   10                  15

Val Glu Tyr Leu Asp Asp Arg Asn Thr Phe Arg His Ser Val Val Val
            20                  25                  30

Pro Tyr Glu Pro Pro Glu Val Gly Ser Asp Cys Thr Thr Ile His Tyr
        35                  40                  45

Asn Tyr Met Cys Asn Ser Ser Cys Met Gly Gly Met Asn Arg Arg Pro
    50                  55                  60

Ile Leu Thr Ile Ile Thr Leu Glu Asp Ser Ser Gly Asn Leu Leu Gly
65                  70                  75                  80

Arg Asn Ser Phe Glu Val Arg Val Cys Ala Cys Pro Gly Arg Asp Arg
                85                  90                  95

Arg Thr Glu Glu Glu Asn Leu Arg Lys Lys Gly Glu Pro His His Glu
            100                 105                 110

Leu Pro Pro Gly Ser Thr Lys Arg Ala Leu Pro Asn Asn Thr Ser Ser
        115                 120                 125

Ser Pro Gln Pro Lys Lys Lys Pro Leu Asp Gly Glu Tyr Phe Thr Leu
    130                 135                 140

Gln Ile Arg Gly Arg Glu Arg Phe Glu Met Phe Arg Glu Leu Asn Glu
145                 150                 155                 160

Ala Leu Glu Leu Lys Asp Ala Gln Ala Gly Lys Glu Pro Gly Gly Ser
                165                 170                 175

Arg Ala His Ser Ser His Leu Lys Ser Lys Lys Gly Gln Ser Thr Ser
            180                 185                 190

Arg His Lys Lys Leu Met Phe Lys Thr Glu Gly Pro Asp Ser Asp
        195                 200                 205

<210> SEQ ID NO 4
<211> LENGTH: 110
<212> TYPE: PRT
<213> ORGANISM: Homo Sapiens

<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg
            100                 105                 110

<210> SEQ ID NO 5
<211> LENGTH: 210
<212> TYPE: PRT
<213> ORGANISM: Homo Sapiens -continued

```
<400> SEQUENCE: 5

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn
    210

<210> SEQ ID NO 6
<211> LENGTH: 312
<212> TYPE: PRT
<213> ORGANISM: Homo Sapiens

<400> SEQUENCE: 6

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155
```

```
            145                 150                 155                 160
Ala Ile Tyr Lys Gln Ser Gln His Met Thr Glu Val Val Arg Arg Cys
                165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
            195                 200                 205
Arg Asn Thr Phe Arg His Ser Val Val Pro Tyr Glu Pro Pro Glu
        210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                245                 250                 255
Leu Glu Asp Ser Ser Gly Asn Leu Leu Gly Arg Asn Ser Phe Glu Val
                260                 265                 270
Arg Val Cys Ala Cys Pro Gly Arg Asp Arg Arg Thr Glu Glu Glu Asn
                275                 280                 285
Leu Arg Lys Lys Gly Glu Pro His His Glu Leu Pro Pro Gly Ser Thr
        290                 295                 300
Lys Arg Ala Leu Pro Asn Asn Thr
305                 310

<210> SEQ ID NO 7
<211> LENGTH: 323
<212> TYPE: PRT
<213> ORGANISM: Homo Sapiens

<400> SEQUENCE: 7

Met Glu Glu Pro Gln Ser Asp Pro Ser Val Pro Pro Leu Ser Gln
1               5                   10                  15
Glu Thr Phe Ser Asp Leu Trp Lys Leu Leu Pro Glu Asn Asn Val Leu
                20                  25                  30
Ser Pro Leu Pro Ser Gln Ala Met Asp Asp Leu Met Leu Ser Pro Asp
                35                  40                  45
Asp Ile Glu Gln Trp Phe Thr Glu Asp Pro Gly Pro Asp Glu Ala Pro
        50                  55                  60
Arg Met Pro Glu Ala Ala Pro Pro Val Ala Pro Ala Pro Ala Ala Pro
65                  70                  75                  80
Thr Pro Ala Ala Pro Ala Pro Ala Pro Ser Trp Pro Leu Ser Ser Ser
                85                  90                  95
Val Pro Ser Gln Lys Thr Tyr Gln Gly Ser Tyr Gly Phe Arg Leu Gly
                100                 105                 110
Phe Leu His Ser Gly Thr Ala Lys Ser Val Thr Cys Thr Tyr Ser Pro
                115                 120                 125
Ala Leu Asn Lys Met Phe Cys Gln Leu Ala Lys Thr Cys Pro Val Gln
        130                 135                 140
Leu Trp Val Asp Ser Thr Pro Pro Pro Gly Thr Arg Val Arg Ala Met
145                 150                 155                 160
Ala Ile Tyr Lys Gln Ser Gln His Met Thr Glu Val Val Arg Arg Cys
                165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
            195                 200                 205
Arg Asn Thr Phe Arg His Ser Val Val Val Pro Tyr Glu Pro Pro Glu
```

```
                210                 215                 220
Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
                275                 280                 285

Leu Arg Lys Lys Gly Glu Pro His His Glu Leu Pro Pro Gly Ser Thr
                290                 295                 300

Lys Arg Ala Leu Pro Asn Asn Thr Ser Ser Ser Pro Gln Pro Lys Lys
305                 310                 315                 320

Lys Pro Leu

<210> SEQ ID NO 8
<211> LENGTH: 343
<212> TYPE: PRT
<213> ORGANISM: Homo Sapiens

<400> SEQUENCE: 8

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
                35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
                115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
                180                 185                 190

His Leu Ile Arg Val Glu Gly Asn Leu Arg Val Glu Tyr Leu Asp Asp
                195                 200                 205

Arg Asn Thr Phe Arg His Ser Val Val Val Pro Tyr Glu Pro Pro Glu
                210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270
```

```
Arg Val Cys Ala Cys Pro Gly Arg Asp Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu
            340

<210> SEQ ID NO 9
<211> LENGTH: 355
<212> TYPE: PRT
<213> ORGANISM: Homo Sapiens

<400> SEQUENCE: 9

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
 50                 55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Thr Glu Glu Glu Asn
        275                 280                 285

Leu Arg Lys Lys Gly Glu Pro His His Glu Leu Pro Pro Gly Ser Thr
290                 295                 300
```

```
Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
                340                 345                 350

Ala Gln Ala
        355

<210> SEQ ID NO 10
<211> LENGTH: 165
<212> TYPE: PRT
<213> ORGANISM: Homo Sapiens

<400> SEQUENCE: 10

Leu Trp Lys Leu Leu Pro Glu Asn Asn Val Leu Ser Pro Leu Pro Ser
1               5                   10                  15

Gln Ala Met Asp Asp Leu Met Leu Ser Pro Asp Asp Ile Glu Gln Trp
            20                  25                  30

Phe Thr Glu Asp Pro Gly Pro Asp Glu Ala Pro Arg Met Pro Glu Ala
            35                  40                  45

Ala Pro Pro Val Ala Pro Ala Pro Ala Ala Pro Thr Pro Ala Ala Pro
    50                  55                  60

Ala Pro Ala Pro Ser Trp Pro Leu Ser Ser Val Pro Ser Gln Lys
65                  70                  75                  80

Thr Tyr Gln Gly Ser Tyr Gly Phe Arg Leu Gly Phe Leu His Ser Gly
                85                  90                  95

Thr Ala Lys Ser Val Thr Cys Thr Tyr Ser Pro Ala Leu Asn Lys Met
            100                 105                 110

Phe Cys Gln Leu Ala Lys Thr Cys Pro Val Gln Leu Trp Val Asp Ser
        115                 120                 125

Thr Pro Pro Pro Gly Thr Arg Val Arg Ala Met Ala Ile Tyr Lys Gln
    130                 135                 140

Ser Gln His Met Thr Glu Val Val Arg Arg Cys Pro His His Glu Arg
145                 150                 155                 160

Cys Ser Asp Ser Asp
                165

<210> SEQ ID NO 11
<211> LENGTH: 372
<212> TYPE: PRT
<213> ORGANISM: Homo Sapiens

<400> SEQUENCE: 11

Leu Trp Lys Leu Leu Pro Glu Asn Asn Val Leu Ser Pro Leu Pro Ser
1               5                   10                  15

Gln Ala Met Asp Asp Leu Met Leu Ser Pro Asp Asp Ile Glu Gln Trp
            20                  25                  30

Phe Thr Glu Asp Pro Gly Pro Asp Glu Ala Pro Arg Met Pro Glu Ala
            35                  40                  45

Ala Pro Pro Val Ala Pro Ala Pro Ala Ala Pro Thr Pro Ala Ala Pro
    50                  55                  60

Ala Pro Ala Pro Ser Trp Pro Leu Ser Ser Val Pro Ser Gln Lys
65                  70                  75                  80

Thr Tyr Gln Gly Ser Tyr Gly Phe Arg Leu Gly Phe Leu His Ser Gly
                85                  90                  95
```

```
Thr Ala Lys Ser Val Thr Cys Thr Tyr Ser Pro Ala Leu Asn Lys Met
            100                 105                 110

Phe Cys Gln Leu Ala Lys Thr Cys Pro Val Gln Leu Trp Val Asp Ser
        115                 120                 125

Thr Pro Pro Gly Thr Arg Val Arg Ala Met Ala Ile Tyr Lys Gln
    130                 135                 140

Ser Gln His Met Thr Glu Val Val Arg Cys Pro His His Glu Arg
145                 150                 155                 160

Cys Ser Asp Ser Asp Gly Leu Ala Pro Pro Gln His Leu Ile Arg Val
                165                 170                 175

Glu Gly Asn Leu Arg Val Glu Tyr Leu Asp Asp Arg Asn Thr Phe Arg
            180                 185                 190

His Ser Val Val Val Pro Tyr Glu Pro Pro Glu Val Gly Ser Asp Cys
        195                 200                 205

Thr Thr Ile His Tyr Asn Tyr Met Cys Asn Ser Ser Cys Met Gly Gly
    210                 215                 220

Met Asn Arg Arg Pro Ile Leu Thr Ile Ile Thr Leu Glu Asp Ser Ser
225                 230                 235                 240

Gly Asn Leu Leu Gly Arg Asn Ser Phe Glu Val Arg Val Cys Ala Cys
                245                 250                 255

Pro Gly Arg Asp Arg Arg Thr Glu Glu Glu Asn Leu Arg Lys Lys Gly
            260                 265                 270

Glu Pro His His Glu Leu Pro Pro Gly Ser Thr Lys Arg Ala Leu Pro
        275                 280                 285

Asn Asn Thr Ser Ser Ser Pro Gln Pro Lys Lys Lys Pro Leu Asp Gly
    290                 295                 300

Glu Tyr Phe Thr Leu Gln Ile Arg Gly Arg Glu Arg Phe Glu Met Phe
305                 310                 315                 320

Arg Glu Leu Asn Glu Ala Leu Glu Leu Lys Asp Ala Gln Ala Gly Lys
                325                 330                 335

Glu Pro Gly Gly Ser Arg Ala His Ser Ser His Leu Lys Ser Lys Lys
            340                 345                 350

Gly Gln Ser Thr Ser Arg His Lys Lys Leu Met Phe Lys Thr Glu Gly
        355                 360                 365

Pro Asp Ser Asp
    370

<210> SEQ ID NO 12
<211> LENGTH: 311
<212> TYPE: PRT
<213> ORGANISM: Homo Sapiens

<400> SEQUENCE: 12

Ala Ala Pro Ala Pro Ala Pro Ser Trp Pro Leu Ser Ser Ser Val Pro
1               5                   10                  15

Ser Gln Lys Thr Tyr Gln Gly Ser Tyr Gly Phe Arg Leu Gly Phe Leu
            20                  25                  30

His Ser Gly Thr Ala Lys Ser Val Thr Cys Thr Tyr Ser Pro Ala Leu
        35                  40                  45

Asn Lys Met Phe Cys Gln Leu Ala Lys Thr Cys Pro Val Gln Leu Trp
    50                  55                  60

Val Asp Ser Thr Pro Pro Gly Thr Arg Val Arg Ala Met Ala Ile
65                  70                  75                  80

Tyr Lys Gln Ser Gln His Met Thr Glu Val Val Arg Arg Cys Pro His
                85                  90                  95
```

His Glu Arg Cys Ser Asp Ser Asp Gly Leu Ala Pro Pro Gln His Leu
            100                 105                 110

Ile Arg Val Glu Gly Asn Leu Arg Val Glu Tyr Leu Asp Asp Arg Asn
            115                 120                 125

Thr Phe Arg His Ser Val Val Val Pro Tyr Glu Pro Pro Glu Val Gly
            130                 135                 140

Ser Asp Cys Thr Thr Ile His Tyr Asn Tyr Met Cys Asn Ser Ser Cys
145                 150                 155                 160

Met Gly Gly Met Asn Arg Arg Pro Ile Leu Thr Ile Ile Thr Leu Glu
                165                 170                 175

Asp Ser Ser Gly Asn Leu Leu Gly Arg Asn Ser Phe Glu Val Arg Val
            180                 185                 190

Cys Ala Cys Pro Gly Arg Asp Arg Arg Thr Glu Glu Glu Asn Leu Arg
            195                 200                 205

Lys Lys Gly Glu Pro His His Glu Leu Pro Pro Gly Ser Thr Lys Arg
            210                 215                 220

Ala Leu Pro Asn Asn Thr Ser Ser Ser Pro Gln Pro Lys Lys Lys Pro
225                 230                 235                 240

Leu Asp Gly Glu Tyr Phe Thr Leu Gln Ile Arg Gly Arg Glu Arg Phe
                245                 250                 255

Glu Met Phe Arg Glu Leu Asn Glu Ala Leu Glu Leu Lys Asp Ala Gln
            260                 265                 270

Ala Gly Lys Glu Pro Gly Gly Ser Arg Ala His Ser Ser His Leu Lys
            275                 280                 285

Ser Lys Lys Gly Gln Ser Thr Ser Arg His Lys Lys Leu Met Phe Lys
290                 295                 300

Thr Glu Gly Pro Asp Ser Asp
305                 310

<210> SEQ ID NO 13
<211> LENGTH: 301
<212> TYPE: PRT
<213> ORGANISM: Homo Sapiens

<400> SEQUENCE: 13

Leu Ser Ser Ser Val Pro Ser Gln Lys Thr Tyr Gln Gly Ser Tyr Gly
1               5                   10                  15

Phe Arg Leu Gly Phe Leu His Ser Gly Thr Ala Lys Ser Val Thr Cys
            20                  25                  30

Thr Tyr Ser Pro Ala Leu Asn Lys Met Phe Cys Gln Leu Ala Lys Thr
            35                  40                  45

Cys Pro Val Gln Leu Trp Val Asp Ser Thr Pro Pro Pro Gly Thr Arg
50                  55                  60

Val Arg Ala Met Ala Ile Tyr Lys Gln Ser Gln His Met Thr Glu Val
65                  70                  75                  80

Val Arg Arg Cys Pro His His Glu Arg Cys Ser Asp Ser Asp Gly Leu
                85                  90                  95

Ala Pro Pro Gln His Leu Ile Arg Val Glu Gly Asn Leu Arg Val Glu
            100                 105                 110

Tyr Leu Asp Asp Arg Asn Thr Phe Arg His Ser Val Val Val Pro Tyr
            115                 120                 125

Glu Pro Pro Glu Val Gly Ser Asp Cys Thr Thr Ile His Tyr Asn Tyr
            130                 135                 140

Met Cys Asn Ser Ser Cys Met Gly Gly Met Asn Arg Arg Pro Ile Leu
145                 150                 155                 160

```
Thr Ile Ile Thr Leu Glu Asp Ser Ser Gly Asn Leu Leu Gly Arg Asn
            165                 170                 175

Ser Phe Glu Val Arg Val Cys Ala Cys Pro Gly Arg Asp Arg Arg Thr
            180                 185                 190

Glu Glu Glu Asn Leu Arg Lys Lys Gly Glu Pro His His Glu Leu Pro
            195                 200                 205

Pro Gly Ser Thr Lys Arg Ala Leu Pro Asn Asn Thr Ser Ser Ser Pro
            210                 215                 220

Gln Pro Lys Lys Lys Pro Leu Asp Gly Glu Tyr Phe Thr Leu Gln Ile
225                 230                 235                 240

Arg Gly Arg Glu Arg Phe Glu Met Phe Arg Glu Leu Asn Glu Ala Leu
            245                 250                 255

Glu Leu Lys Asp Ala Gln Ala Gly Lys Glu Pro Gly Gly Ser Arg Ala
            260                 265                 270

His Ser Ser His Leu Lys Ser Lys Lys Gly Gln Ser Thr Ser Arg His
            275                 280                 285

Lys Lys Leu Met Phe Lys Thr Glu Gly Pro Asp Ser Asp
            290                 295                 300

<210> SEQ ID NO 14
<211> LENGTH: 219
<212> TYPE: PRT
<213> ORGANISM: Homo Sapiens

<400> SEQUENCE: 14

Ser Ser Ser Val Pro Ser Gln Lys Thr Tyr Gln Gly Ser Tyr Gly Phe
1               5                   10                  15

Arg Leu Gly Phe Leu His Ser Gly Thr Ala Lys Ser Val Thr Cys Thr
            20                  25                  30

Tyr Ser Pro Ala Leu Asn Lys Met Phe Cys Gln Leu Ala Lys Thr Cys
            35                  40                  45

Pro Val Gln Leu Trp Val Asp Ser Thr Pro Pro Gly Thr Arg Val
        50                  55                  60

Arg Ala Met Ala Ile Tyr Lys Gln Ser Gln His Met Thr Glu Val Val
65                  70                  75                  80

Arg Arg Cys Pro His His Glu Arg Cys Ser Asp Ser Asp Gly Leu Ala
            85                  90                  95

Pro Pro Gln His Leu Ile Arg Val Glu Gly Asn Leu Arg Val Glu Tyr
            100                 105                 110

Leu Asp Asp Arg Asn Thr Phe Arg His Ser Val Val Val Pro Tyr Glu
            115                 120                 125

Pro Pro Glu Val Gly Ser Asp Cys Thr Thr Ile His Tyr Asn Tyr Met
            130                 135                 140

Cys Asn Ser Ser Cys Met Gly Gly Met Asn Arg Arg Pro Ile Leu Thr
145                 150                 155                 160

Ile Ile Thr Leu Glu Asp Ser Ser Gly Asn Leu Leu Gly Arg Asn Ser
            165                 170                 175

Phe Glu Val Arg Val Cys Ala Cys Pro Gly Arg Asp Arg Arg Thr Glu
            180                 185                 190

Glu Glu Asn Leu Arg Lys Lys Gly Glu Pro His His Glu Leu Pro Pro
            195                 200                 205

Gly Ser Thr Lys Arg Ala Leu Pro Asn Asn Thr
            210                 215

<210> SEQ ID NO 15
<211> LENGTH: 294
```

<212> TYPE: PRT
<213> ORGANISM: Homo Sapiens

<400> SEQUENCE: 15

```
Gln Lys Thr Tyr Gln Gly Ser Tyr Gly Phe Arg Leu Gly Phe Leu His
 1               5                  10                  15

Ser Gly Thr Ala Lys Ser Val Thr Cys Thr Tyr Ser Pro Ala Leu Asn
             20                  25                  30

Lys Met Phe Cys Gln Leu Ala Lys Thr Cys Pro Val Gln Leu Trp Val
         35                  40                  45

Asp Ser Thr Pro Pro Gly Thr Arg Val Arg Ala Met Ala Ile Tyr
 50                  55                  60

Lys Gln Ser Gln His Met Thr Glu Val Val Arg Arg Cys Pro His His
 65                  70                  75                  80

Glu Arg Cys Ser Asp Ser Asp Gly Leu Ala Pro Pro Gln His Leu Ile
                 85                  90                  95

Arg Val Glu Gly Asn Leu Arg Val Glu Tyr Leu Asp Asp Arg Asn Thr
             100                 105                 110

Phe Arg His Ser Val Val Val Pro Tyr Glu Pro Pro Glu Val Gly Ser
         115                 120                 125

Asp Cys Thr Thr Ile His Tyr Asn Tyr Met Cys Asn Ser Ser Cys Met
130                 135                 140

Gly Gly Met Asn Arg Arg Pro Ile Leu Thr Ile Ile Thr Leu Glu Asp
145                 150                 155                 160

Ser Ser Gly Asn Leu Leu Gly Arg Asn Ser Phe Glu Val Arg Val Cys
                 165                 170                 175

Ala Cys Pro Gly Arg Asp Arg Arg Thr Glu Glu Asn Leu Arg Lys
             180                 185                 190

Lys Gly Glu Pro His His Glu Leu Pro Pro Gly Ser Thr Lys Arg Ala
         195                 200                 205

Leu Pro Asn Asn Thr Ser Ser Pro Gln Pro Lys Lys Lys Pro Leu
210                 215                 220

Asp Gly Glu Tyr Phe Thr Leu Gln Ile Arg Gly Arg Glu Arg Phe Glu
225                 230                 235                 240

Met Phe Arg Glu Leu Asn Glu Ala Leu Glu Leu Lys Asp Ala Gln Ala
                 245                 250                 255

Gly Lys Glu Pro Gly Gly Ser Arg Ala His Ser Ser His Leu Lys Ser
             260                 265                 270

Lys Lys Gly Gln Ser Thr Ser Arg His Lys Lys Leu Met Phe Lys Thr
         275                 280                 285

Glu Gly Pro Asp Ser Asp
    290
```

<210> SEQ ID NO 16
<211> LENGTH: 76
<212> TYPE: PRT
<213> ORGANISM: Homo Sapiens

<400> SEQUENCE: 16

```
Pro Lys Lys Lys Pro Leu Asp Gly Glu Tyr Phe Thr Leu Gln Ile Arg
 1               5                  10                  15

Gly Arg Glu Arg Phe Glu Met Phe Arg Glu Leu Asn Glu Ala Leu Glu
             20                  25                  30

Leu Lys Asp Ala Gln Ala Gly Lys Glu Pro Gly Gly Ser Arg Ala His
         35                  40                  45

Ser Ser His Leu Lys Ser Lys Lys Gly Gln Ser Thr Ser Arg His Lys
```

```
                50                  55                  60
Lys Leu Met Phe Lys Thr Glu Gly Pro Asp Ser Asp
 65                  70                  75

<210> SEQ ID NO 17
<211> LENGTH: 54
<212> TYPE: PRT
<213> ORGANISM: Homo Sapiens

<400> SEQUENCE: 17

Met Phe Arg Glu Leu Asn Glu Ala Leu Glu Leu Lys Asp Ala Gln Ala
  1               5                  10                  15

Gly Lys Glu Pro Gly Gly Ser Arg Ala His Ser Ser His Leu Lys Ser
                 20                  25                  30

Lys Lys Gly Gln Ser Thr Ser Arg His Lys Lys Leu Met Phe Lys Thr
             35                  40                  45

Glu Gly Pro Asp Ser Asp
         50

<210> SEQ ID NO 18
<211> LENGTH: 37
<212> TYPE: PRT
<213> ORGANISM: Homo Sapiens

<400> SEQUENCE: 18

Met Thr Ala Lys Ser Val Thr Cys Thr Tyr Ser Pro Ala Leu Asn Lys
  1               5                  10                  15

Met Phe Cys Gln Leu Ala Lys Thr Cys Pro Val Val Arg Arg Cys
                 20                  25                  30

Pro His His Glu Arg
         35

<210> SEQ ID NO 19
<211> LENGTH: 164
<212> TYPE: PRT
<213> ORGANISM: Homo Sapiens

<400> SEQUENCE: 19

Met Ser Glu Pro Ala Gly Asp Val Arg Gln Asn Pro Cys Gly Ser Lys
  1               5                  10                  15

Ala Cys Arg Arg Leu Phe Gly Pro Val Asp Ser Glu Gln Leu Ser Arg
                 20                  25                  30

Asp Cys Asp Ala Leu Met Ala Gly Cys Ile Gln Glu Ala Arg Glu Arg
             35                  40                  45

Trp Asn Phe Asp Phe Val Thr Glu Thr Pro Leu Glu Gly Asp Phe Ala
 50                  55                  60

Trp Glu Arg Val Arg Gly Leu Gly Leu Pro Lys Leu Tyr Leu Pro Thr
 65                  70                  75                  80

Gly Pro Arg Arg Gly Arg Asp Glu Leu Gly Gly Arg Arg Pro Gly
                 85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
            115                 120                 125

Gly Ser Pro Gly Gly Pro Gly Asp Ser Gln Gly Arg Lys Arg Arg Gln
            130                 135                 140

Thr Ser Met Thr Asp Phe Tyr His Ser Lys Arg Arg Leu Ile Phe Ser
145                 150                 155                 160
```

Lys Arg Lys Pro

<210> SEQ ID NO 20
<211> LENGTH: 78
<212> TYPE: PRT
<213> ORGANISM: Homo Sapiens

<400> SEQUENCE: 20

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu
65                  70                  75

<210> SEQ ID NO 21
<211> LENGTH: 93
<212> TYPE: PRT
<213> ORGANISM: Homo Sapiens

<400> SEQUENCE: 21

Gly Leu Pro Lys Leu Tyr Leu Pro Thr Gly Pro Arg Arg Gly Arg Asp
1               5                   10                  15

Glu Leu Gly Gly Gly Arg Arg Pro Gly Thr Ser Pro Ala Leu Leu Gln
            20                  25                  30

Gly Thr Ala Glu Glu Asp His Val Asp Leu Ser Leu Ser Cys Thr Leu
        35                  40                  45

Val Pro Arg Ser Gly Glu Gln Ala Glu Gly Ser Pro Gly Gly Pro Gly
    50                  55                  60

Asp Ser Gln Gly Arg Lys Arg Arg Gln Thr Ser Met Thr Asp Phe Tyr
65                  70                  75                  80

His Ser Lys Arg Arg Leu Ile Phe Ser Lys Arg Lys Pro
                85                  90

<210> SEQ ID NO 22
<211> LENGTH: 198
<212> TYPE: PRT
<213> ORGANISM: Homo Sapiens

<400> SEQUENCE: 22

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
                100                 105                 110

```
Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
            165                 170                 175

Gly Ser Pro Asn Ala Gly Ser Val Glu Gln Thr Pro Lys Lys Pro Gly
            180                 185                 190

Leu Arg Arg Arg Gln Thr
            195

<210> SEQ ID NO 23
<211> LENGTH: 101
<212> TYPE: PRT
<213> ORGANISM: Homo Sapiens

<400> SEQUENCE: 23

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val
            100

<210> SEQ ID NO 24
<211> LENGTH: 104
<212> TYPE: PRT
<213> ORGANISM: Homo Sapiens

<400> SEQUENCE: 24

Pro Lys Gly Ala Cys Lys Val Pro Ala Gln Glu Ser Gln Asp Val Ser
1               5                   10                  15

Gly Ser Arg Pro Ala Ala Pro Leu Ile Gly Ala Pro Ala Asn Ser Glu
            20                  25                  30

Asp Thr His Leu Val Asp Pro Lys Thr Asp Pro Ser Asp Ser Gln Thr
        35                  40                  45

Gly Leu Ala Glu Gln Cys Ala Gly Ile Arg Lys Arg Pro Ala Thr Asp
    50                  55                  60

Asp Ser Ser Thr Gln Asn Lys Arg Ala Asn Arg Thr Glu Glu Asn Val
65                  70                  75                  80

Ser Asp Gly Ser Pro Asn Ala Gly Ser Val Glu Gln Thr Pro Lys Lys
                85                  90                  95

Pro Gly Leu Arg Arg Arg Gln Thr
            100

<210> SEQ ID NO 25
<211> LENGTH: 636
<212> TYPE: PRT
```

<213> ORGANISM: Homo Sapiens

<400> SEQUENCE: 25

```
Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65              70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145             150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Pro Tyr
225             230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Met Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305             310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Gln Leu Leu Gln Arg Pro Ser
385             390                 395                 400

His Leu Gln Pro Pro Ser Tyr Gly Pro Val Leu Ser Pro Met Asn Lys
```

```
                405                 410                 415
Val His Gly Gly Met Asn Lys Leu Pro Ser Val Asn Gln Leu Val Gly
            420                 425                 430

Gln Pro Pro His Ser Ser Ala Ala Thr Pro Asn Leu Gly Pro Val
        435                 440                 445

Gly Pro Gly Met Leu Asn Asn His Gly His Ala Val Pro Ala Asn Gly
        450                 455                 460

Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Ser Phe
                485                 490                 495

Leu Thr Gly Leu Gly Cys Pro Asn Cys Ile Glu Tyr Phe Thr Ser Gln
        500                 505                 510

Gly Leu Gln Ser Ile Tyr His Leu Gln Asn Leu Thr Ile Glu Asp Leu
        515                 520                 525

Gly Ala Leu Lys Ile Pro Glu Gln Tyr Arg Met Thr Ile Trp Arg Gly
        530                 535                 540

Leu Gln Asp Leu Lys Gln Gly His Asp Tyr Ser Thr Ala Gln Leu
545                 550                 555                 560

Leu Arg Ser Ser Asn Ala Ala Thr Ile Ser Ile Gly Ser Gly Glu
                565                 570                 575

Leu Gln Arg Gln Arg Val Met Glu Ala Val His Phe Arg Val Arg His
        580                 585                 590

Thr Ile Thr Ile Pro Asn Arg Gly Gly Pro Gly Gly Pro Asp Glu
                595                 600                 605

Trp Ala Asp Phe Gly Phe Asp Leu Pro Asp Cys Lys Ala Arg Lys Gln
        610                 615                 620

Pro Ile Lys Glu Glu Phe Thr Glu Ala Glu Ile His
625                 630                 635

<210> SEQ ID NO 26
<211> LENGTH: 319
<212> TYPE: PRT
<213> ORGANISM: Homo Sapiens

<400> SEQUENCE: 26

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
```

-continued

```
            145                 150                 155                 160
Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
            180                 185                 190

Arg Cys Pro Asn His Glu Leu Gly Arg Asp Phe Asn Glu Gly Gln Ser
            195                 200                 205

Ala Pro Ala Ser His Leu Ile Arg Val Glu Gly Asn Asn Leu Ser Gln
        210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Met Arg Asp Gly Gln Val Leu Gly Arg Arg
            275                 280                 285

Ser Phe Glu Gly Arg Ile Cys Ala Cys Pro Gly Arg Asp Arg Lys Ala
        290                 295                 300

Asp Glu Asp His Tyr Arg Glu Gln Gln Ala Leu Asn Glu Ser Ser
305                 310                 315

<210> SEQ ID NO 27
<211> LENGTH: 318
<212> TYPE: PRT
<213> ORGANISM: Homo Sapiens

<400> SEQUENCE: 27

Ser Ala Lys Asn Gly Ala Ala Ser Lys Arg Ala Phe Lys Gln Ser Pro
1               5                   10                  15

Pro Ala Val Pro Ala Leu Gly Ala Gly Val Lys Lys Arg Arg His Gly
            20                  25                  30

Asp Glu Asp Thr Tyr Tyr Leu Gln Val Arg Gly Arg Glu Asn Phe Glu
        35                  40                  45

Ile Leu Met Lys Leu Lys Glu Ser Leu Glu Leu Met Glu Leu Val Pro
    50                  55                  60

Gln Pro Leu Val Asp Ser Tyr Arg Gln Gln Gln Leu Leu Gln Arg
65                  70                  75                  80

Pro Ser His Leu Gln Pro Pro Ser Tyr Gly Pro Val Leu Ser Pro Met
                85                  90                  95

Asn Lys Val His Gly Gly Met Asn Lys Leu Pro Ser Val Asn Gln Leu
            100                 105                 110

Val Gly Gln Pro Pro His Ser Ser Ala Ala Thr Pro Asn Leu Gly
        115                 120                 125

Pro Val Gly Pro Gly Met Leu Asn Asn His Gly His Ala Val Pro Ala
130                 135                 140

Asn Gly Glu Met Ser Ser His Ser Ala Gln Ser Met Val Ser Gly
145                 150                 155                 160

Ser His Cys Thr Pro Pro Pro Tyr His Ala Asp Pro Ser Leu Val
                165                 170                 175

Ser Phe Leu Thr Gly Leu Gly Cys Pro Asn Cys Ile Glu Tyr Phe Thr
            180                 185                 190

Ser Gln Gly Leu Gln Ser Ile Tyr His Leu Gln Asn Leu Thr Ile Glu
        195                 200                 205

Asp Leu Gly Ala Leu Lys Ile Pro Glu Gln Tyr Arg Met Thr Ile Trp
```

```
                210                 215                 220
Arg Gly Leu Gln Asp Leu Lys Gln Gly His Asp Tyr Ser Thr Ala Gln
225                 230                 235                 240

Gln Leu Leu Arg Ser Ser Asn Ala Ala Thr Ile Ser Ile Gly Gly Ser
                245                 250                 255

Gly Glu Leu Gln Arg Gln Arg Val Met Glu Ala Val His Phe Arg Val
                260                 265                 270

Arg His Thr Ile Thr Ile Pro Asn Arg Gly Pro Gly Gly Pro
                275                 280                 285

Asp Glu Trp Ala Asp Phe Gly Phe Asp Leu Pro Asp Cys Lys Ala Arg
290                 295                 300

Lys Gln Pro Ile Lys Glu Glu Phe Thr Glu Ala Glu Ile His
305                 310                 315

<210> SEQ ID NO 28
<211> LENGTH: 680
<212> TYPE: PRT
<213> ORGANISM: Homo Sapiens

<400> SEQUENCE: 28

Met Asn Phe Glu Thr Ser Arg Cys Ala Thr Leu Gln Tyr Cys Pro Asp
  1               5                  10                  15

Pro Tyr Ile Gln Arg Phe Val Glu Thr Pro Ala His Phe Ser Trp Lys
                 20                  25                  30

Glu Ser Tyr Tyr Arg Ser Thr Met Ser Gln Ser Thr Gln Thr Asn Glu
             35                  40                  45

Phe Leu Ser Pro Glu Val Phe Gln His Ile Trp Asp Phe Leu Glu Gln
 50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
                 85                  90                  95

Arg Met Gln Asp Ser Asp Leu Ser Asp Pro Met Trp Pro Gln Tyr Thr
                100                 105                 110

Asn Leu Gly Leu Leu Asn Ser Met Asp Gln Gln Ile Gln Asn Gly Ser
            115                 120                 125

Ser Ser Thr Ser Pro Tyr Asn Thr Asp His Ala Gln Asn Ser Val Thr
        130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Gln Gly Ala Val
210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
```

```
                275                 280                 285
Pro Tyr Glu Pro Pro Gln Val Gly Thr Glu Phe Thr Thr Val Leu Tyr
290                 295                 300

Asn Phe Met Cys Asn Ser Ser Cys Val Gly Met Asn Arg Arg Pro
305                 310                 315                 320

Ile Leu Ile Ile Val Thr Leu Glu Thr Arg Asp Gly Gln Val Leu Gly
            325                 330                 335

Arg Arg Cys Phe Glu Ala Arg Ile Cys Ala Cys Pro Gly Arg Asp Arg
                340                 345                 350

Lys Ala Asp Glu Asp Ser Ile Arg Lys Gln Gln Val Ser Asp Ser Thr
            355                 360                 365

Lys Asn Gly Asp Gly Thr Lys Arg Pro Phe Arg Gln Asn Thr His Gly
370                 375                 380

Ile Gln Met Thr Ser Ile Lys Lys Arg Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln His Gln His Leu Leu Gln
            435                 440                 445

Lys Gln Thr Ser Ile Gln Ser Pro Ser Ser Tyr Gly Asn Ser Ser Pro
450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
            515                 520                 525

Leu Ser Met Pro Ser Thr Ser His Cys Thr Pro Pro Pro Pro Tyr Pro
530                 535                 540

Thr Asp Cys Ser Ile Val Ser Phe Leu Ala Arg Leu Gly Cys Ser Ser
545                 550                 555                 560

Cys Leu Asp Tyr Phe Thr Thr Gln Gly Leu Thr Thr Ile Tyr Gln Ile
                565                 570                 575

Glu His Tyr Ser Met Asp Asp Leu Ala Ser Leu Lys Ile Pro Glu Gln
            580                 585                 590

Phe Arg His Ala Ile Trp Lys Gly Ile Leu Asp His Arg Gln Leu His
            595                 600                 605

Glu Phe Ser Ser Pro Ser His Leu Leu Arg Thr Pro Ser Ser Ala Ser
            610                 615                 620

Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
                645                 650                 655

Glu Trp Asn Asp Phe Asn Phe Asp Met Asp Ala Arg Asn Lys Gln
            660                 665                 670

Gln Arg Ile Lys Glu Glu Gly Glu
675                 680
```